(12) United States Patent
Shi

(10) Patent No.: US 11,583,570 B2
(45) Date of Patent: Feb. 21, 2023

(54) USE OF AUTOINDUCER-RELATED PATHWAY IN INDUCING APOPTOSIS AND ANTI-INFECTIVE THERAPY

(71) Applicant: TSINGHUA UNIVERSITY, Beijing (CN)

(72) Inventor: Yan Shi, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 461 days.

(21) Appl. No.: 16/607,030

(22) PCT Filed: Apr. 24, 2017

(86) PCT No.: PCT/CN2017/081719
§ 371 (c)(1),
(2) Date: Oct. 21, 2019

(87) PCT Pub. No.: WO2018/195727
PCT Pub. Date: Nov. 1, 2018

(65) Prior Publication Data
US 2020/0384078 A1    Dec. 10, 2020

(51) Int. Cl.
*A61K 38/17*     (2006.01)
*A61P 37/04*     (2006.01)
*A61K 31/167*    (2006.01)
*A61K 31/365*    (2006.01)
*A61K 38/00*     (2006.01)

(52) U.S. Cl.
CPC ........ *A61K 38/1793* (2013.01); *A61K 31/167* (2013.01); *A61K 31/365* (2013.01); *A61K 38/005* (2013.01); *A61P 37/04* (2018.01)

(58) Field of Classification Search
CPC .............. A61K 38/1793; A61K 31/167; A61K 31/365; A61K 38/005; A61P 37/04
See application file for complete search history.

(56) References Cited

U.S. PATENT DOCUMENTS

2005/0250841 A1 * 11/2005 Pearson ............... A61K 31/382
514/432
2015/0359888 A1 * 12/2015 Yun ........................ G16H 20/00
600/301

OTHER PUBLICATIONS

Skerrett et al., American Physiological Society, Dec. 31, 1999, L715-L725 (Year: 1999).*

* cited by examiner

*Primary Examiner* — Robert S Cabral
(74) *Attorney, Agent, or Firm* — Platinum Intellectual Property

(57) ABSTRACT

Use of a TNFR1-FADD-caspase8-caspase3 pathway inhibitor in preparation of a medicament for treating an immune system related disease caused by autoinducer, a method for screening a medicament for treating an immune system related disease caused by autoinducer and a method for treating an immune system related disease.

2 Claims, 38 Drawing Sheets a b b a b e f j k a b

USE OF AUTOINDUCER-RELATED PATHWAY IN INDUCING APOPTOSIS AND ANTI-INFECTIVE THERAPY

RELATED APPLICATIONS

This application is a United States National Stage Application filed under 35 U.S.C 371 of PCT Patent Application Serial No. PCT/CN2017/081719, filed Apr. 24, 2017, the disclosure of all of which are hereby incorporated by reference in their entirety.

FIELD

The present disclosure relates to a bio-medicine, and more particularly to use of a TNFR1-FADD-caspase8-caspase3 pathway inhibitor in preparation of a medicament for treating an immune system related disease caused by autoinducer, a method for screening a medicament for treating an immune system related disease caused by autoinducer and a method for treating an immune system related disease.

BACKGROUND

Quorum sensing (QS) is a chemical-based communication mechanism in prokaryotes. An QS autoinducer released by select individuals is sensed by intracellular receptors in other members of the community, leading to collective isogenic autoinducer synthesis and synchronized activities in symbiosis with the host, virulence, and biofilm formation of the community. Pseudomonas aeruginosa (PA) is a pathogen responsible to severe opportunistic infections. In PA, LasR-LasI QS circuit uses N-(3-oxo-dodecanoyl) homoserine lactone (3OC12 HSL or 3OC) as the autoinducer that represents a large family of autoinducers differing mainly at the length of acyl chain. While QS is by design a self-contained microbial circuitry, it has widespread impact in mammalian hosts, ranging from cell death induction, transcriptional control, immune regulation, to inflammation and immune cell death.

As TLRs and NLRs are not involved in their signaling, how QS molecules mediate the diverse host responses remains undefined.

SUMMARY

Embodiments of the present disclosure seek to solve at least one of the problems existing in the prior art to at least some extent, or to provide a consumer with a useful commercial choice.

Here the inventor discovered an unexpected mechanism that ordered lipid domains unique in eukaryotic membrane are dissolvable in the presence of HSLs. This in turn results in a forced expulsion of TNF receptor 1 (TNFR1) into the disordered phase of membrane. The displaced TNFR1 demonstrates higher motion speeds and extended migratory trajectories on live cell membrane, leading to a higher degree of spontaneous trimerization and TNFR1 signaling without external ligand. This distribution shift drives the entire process of caspase 8-caspase 3 axis activation and apoptotic cell death. These findings suggest a previously unknown mechanism how eukaryotic cells sense microbial metabolic products.

According to embodiments of a first broad aspect of the present disclosure, there is provided use of a TNFR1-FADD-caspase8-caspase3 pathway inhibitor in preparation of a medicament for treating an immune system related disease caused by autoinducer. According to the embodiments, autoinducer, such as 3OC12 HSL, can activate immune cell TNFR1-FADD-caspase8-caspase3 pathway and then induce immune cell apoptosis and cause immune system related disease. Furthermore, the inventor discovered that TNFR1-FADD-caspase8-caspase3 pathway inhibitor showed significant therapeutic effect in treating immune system related disease caused by autoinducer.

According to embodiments of present disclosure, the above mentioned use may possess at least one of the following additional features:

According to embodiments of present disclosure, the autoinducer is derived from Pseudomonas aeruginosa. According to the embodiments, the inventor discovered that TNFR1-FADD-caspase8-caspase3 pathway inhibitor showed more significant therapeutic effect in treating immune system related disease caused by autoinducer derived from Pseudomonas aeruginosa.

According to embodiments of present disclosure, the immune system related disease is Pseudomonas aeruginosa infection-related disease. Through experiments, it's found that TNFR1-FADD-caspase8-caspase3 pathway inhibitor showed more significant therapeutic effect in treating Pseudomonas aeruginosa infection-related disease.

According to embodiments of present disclosure, the TNFR1-FADD-caspase8-caspase3 pathway inhibitor is at least one selected from a group consisting of a TNFR1 inhibitor, a TNFR1 trimerization inhibitor, a FADD inhibitor, a caspase inhibitor. The inventor discovered that TNFR1 inhibitor, TNFR1 trimerization inhibitor, FADD inhibitor, caspase inhibitor can bock TNFR1-FADD-caspase8-caspase3 pathway activated by autoinducer effectively. TNFR1 inhibitor, TNFR1 trimerization inhibitor, FADD inhibitor, caspase inhibitor showed more significant therapeutic effect in treating immune system related disease caused by autoinducer.

According to embodiments of present disclosure, the TNFR1 trimerization inhibitor comprises: (a) a competitive inhibitor peptide for TNFR1; or (b) a nucleic acid or construct expressing (a). It was found that blocking TNFR1 trimerization could inhibit TNFR1 activation effectively. It was also found that competitive inhibitor peptide for TNFR1 or nucleic acid or construct expressing the peptide was an effective TNFR1 trimerization inhibitor. The competitive inhibitor peptide for TNFR1 or nucleic acid or construct expressing the peptide showed significant therapeutic effect in treating immune system related disease caused by autoinducer.

According to embodiments of present disclosure, the competitive inhibitor peptide for TNFR1 is TNFR-like T2. Through experiments, it's found that TNFR-like T2 showed more significant effect in inhibiting TNFR1 trimerization.

According to embodiments of present disclosure, the TNFR1 inhibitor comprises at least one selected from a group consisting of a TNFR1 expression inhibitor, a TNFR1 mutant inducer, a TNFR1 functional inhibitor, a TNFR1 functional analog. The TNFR1 inhibitor showed above can inhibit TNFR1 expression or inhibit TNFR1 activating and then prevent apoptosis caused by autoinducer effectively.

According to embodiments of present disclosure, the FADD inhibitor comprises at least one selected from a group consisting of a FADD expression inhibitor, a FADD mutant inducer, a FADD functional inhibitor, a FADD functional analog. The FADD inhibitor showed above can inhibit FADD expression or inhibit FADD activating and then prevent apoptosis caused by autoinducer effectively.

According to embodiments of present disclosure, the caspase inhibitor comprises at least one selected from a group consisting of Z-VAD, Z-DEVD, Z-IETD, Emricasan, a shRNA specific to caspase, an agent inducing deviating away from caspase pathway by activating RIP1. The caspase inhibitor showed above can inhibit caspase expression or inhibit caspase activating and then prevent apoptosis caused by autoinducer effectively.

According to embodiments of present disclosure, the autoinducer is $C_{8~12}$ alkyl acyl homoserine lactone or derivatives thereof. Through experiments, it's found that $C_{8~12}$ alkyl acyl homoserine lactone or derivatives thereof can induce immune cell apoptosis and cause immune system related disease seriously. TNFR1-FADD-caspase8-caspase3 pathway inhibitor showed significant therapeutic effect in treating immune system related disease caused by $C_{8~12}$ alkyl acyl homoserine lactone or derivatives thereof.

According to embodiments of present disclosure, the autoinducer is $C_{12}$ alkyl acyl homoserine lactone or derivatives thereof. The inventor discovered that TNFR1-FADD-caspase8-caspase3 pathway inhibitor showed more significant therapeutic effect in treating immune system related disease caused by $C_{12}$ alkyl acyl homoserine lactone or derivatives thereof.

According to embodiments of a second broad aspect of the present disclosure, there is provided a method for screening a medicament for treating an immune system related disease caused by autoinducer, comprising: (1) contacting a candidate compound with an immune cell; (2) determining at least one of the following prior to and after the contacting: (a) a trimerization level of a cell surface TNFR1; (b) an activation level of a TNFR1-FADD-caspase8-caspase3 pathway, wherein the decrease of the trimerization level of a cell surface TNFR1 or the decrease of the activation level of a TNFR1-FADD-caspase8-caspase3 pathway is an indication for the candidate compound is a medicament for treating an immune system related disease caused by autoinducer. According to the embodiments, the method described above can screen a medicament for treating an immune system related disease caused by autoinducer effectively.

According to embodiments of present disclosure, the above mentioned method may possess at least one of the following additional features:

According to the embodiments of present disclosure, the autoinducer is $C_{8~12}$ alkyl acyl homoserine lactone or derivatives thereof. Through experiments, it's found that $C_{8~12}$ alkyl acyl homoserine lactone or derivatives thereof can significantly induce TNFR1 trimerization and activate TNFR1-FADD-caspase8-caspase3 pathway. The results under the method for screening a medicament for treating an immune system related disease caused by autoinducer, especially by $C_{8~12}$ alkyl acyl homoserine lactone or derivatives thereof are more reliable. The method is more sensitive.

According to the embodiments of present disclosure, the autoinducer is $C_{12}$ alkyl acyl homoserine lactone or derivatives thereof. It was found that The results under the method for screening a medicament for treating an immune system related disease caused by $C_{12}$ alkyl acyl homoserine lactone or derivatives thereof are much more reliable. The method is much more sensitive.

According to embodiments of a third broad aspect of the present disclosure, there is provided use of a method for treating an immune system related disease caused by autoinducer, comprising:

administrating a TNFR1-FADD-caspase8-caspase3 pathway inhibitor to a subject in need thereof. According to the embodiments, autoinducer, such as 3OC12 HSL, can activate immune cell TNFR1-FADD-caspase8-caspase3 pathway and then induce immune cell apoptosis and cause immune system related disease. Furthermore, the inventor discovered that administrating a TNFR1-FADD-caspase8-caspase3 pathway inhibitor to a subject in need thereof showed significant therapeutic effect in treating immune system related disease caused by autoinducer.

According to embodiments of present disclosure, the above mentioned use may possess at least one of the following additional features:

According to embodiments of present disclosure, the autoinducer is derived from *Pseudomonas aeruginosa*. According to the embodiments, the inventor discovered that TNFR1-FADD-caspase8-caspase3 pathway inhibitor showed more significant therapeutic effect in treating immune system related disease caused by autoinducer derived from *Pseudomonas aeruginosa*.

According to embodiments of present disclosure, the immune system related disease is *Pseudomonas aeruginosa* infection-related disease. Through experiments, it's found that TNFR1-FADD-caspase8-caspase3 pathway inhibitor showed more significant therapeutic effect in treating *Pseudomonas aeruginosa* infection-related disease.

According to embodiments of present disclosure, the TNFR1-FADD-caspase8-caspase3 pathway inhibitor is at least one selected from a group consisting of a TNFR1 inhibitor, a TNFR1 trimerization inhibitor, a FADD inhibitor, a caspase inhibitor. The inventor discovered that TNFR1 inhibitor, TNFR1 trimerization inhibitor, FADD inhibitor, caspase inhibitor can bock TNFR1-FADD-caspase8-caspase3 pathway activated by autoinducer effectively. TNFR1 inhibitor, TNFR1 trimerization inhibitor, FADD inhibitor, caspase inhibitor showed more significant therapeutic effect in treating immune system related disease caused by autoinducer.

According to embodiments of present disclosure, the TNFR1 trimerization inhibitor comprises: (a) a competitive inhibitor peptide for TNFR1; or (b) a nucleic acid or construct expressing (a). It was found that blocking TNFR1 trimerization could inhibit TNFR1 activation effectively. It was also found that competitive inhibitor peptide for TNFR1 or nucleic acid or construct expressing the peptide was an effective TNFR1 trimerization inhibitor. The competitive inhibitor peptide for TNFR1 or nucleic acid or construct expressing the peptide showed significant therapeutic effect in treating immune system related disease caused by autoinducer.

According to embodiments of present disclosure, the competitive inhibitor peptide for TNFR1 is TNFR-like T2. Through experiments, it's found that TNFR-like T2 showed more significant effect in inhibiting TNFR1 trimerization.

According to embodiments of present disclosure, the TNFR1 inhibitor comprises at least one selected from a group consisting of a TNFR1 expression inhibitor, a TNFR1 mutant inducer, a TNFR1 functional inhibitor, a TNFR1 functional analog. The TNFR1 inhibitor showed above can inhibit TNFR1 expression or inhibit TNFR1 activating and then prevent apoptosis caused by autoinducer effectively.

According to embodiments of present disclosure, the FADD inhibitor comprises at least one selected from a group consisting of a FADD expression inhibitor, a FADD mutant inducer, a FADD functional inhibitor, a FADD functional analog. The FADD inhibitor showed above can inhibit FADD expression or inhibit FADD activating and then prevent apoptosis caused by autoinducer effectively.

According to embodiments of present disclosure, the caspase inhibitor comprises at least one selected from a group consisting of Z-VAD, Z-DEVD, Z-IETD, Emricasan, a shRNA specific to caspase, an agent inducing deviating away from caspase pathway by activating RIP1. The caspase inhibitor showed above can inhibit caspase expression or inhibit caspase activating and then prevent apoptosis caused by autoinducer effectively.

According to embodiments of present disclosure, the autoinducer is $C_{8-12}$ alkyl acyl homoserine lactone or derivatives thereof. Through experiments, it's found that $C_{8-12}$ alkyl acyl homoserine lactone or derivatives thereof can induce immune cell apoptosis and cause immune system related disease seriously. TNFR1-FADD-caspase8-caspase3 pathway inhibitor showed significant therapeutic effect in treating immune system related disease caused by $C_{8-12}$ alkyl acyl homoserine lactone or derivatives thereof.

According to embodiments of present disclosure, the autoinducer is $C_{12}$ alkyl acyl homoserine lactone or derivatives thereof. The inventor discovered that TNFR1-FADD-caspase8-caspase3 pathway inhibitor showed more significant therapeutic effect in treating immune system related disease caused by $C_{12}$ alkyl acyl homoserine lactone or derivatives thereof.

The above summary of the present disclosure is not intended to describe each disclosed embodiment or every implementation of the present disclosure. The Figures and the detailed description which follow more particularly exemplify illustrative embodiments.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
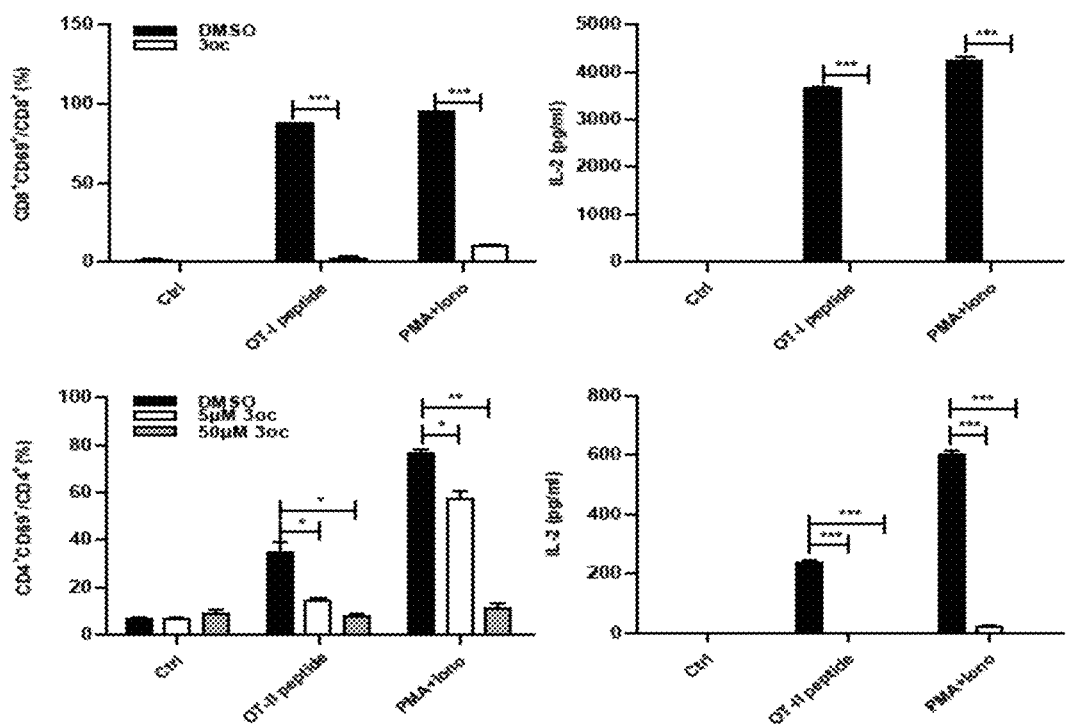
FIG. 1 shows 3OC12 HSL inhibits T cell activation as a consequence of apoptosis.
Figure 1:
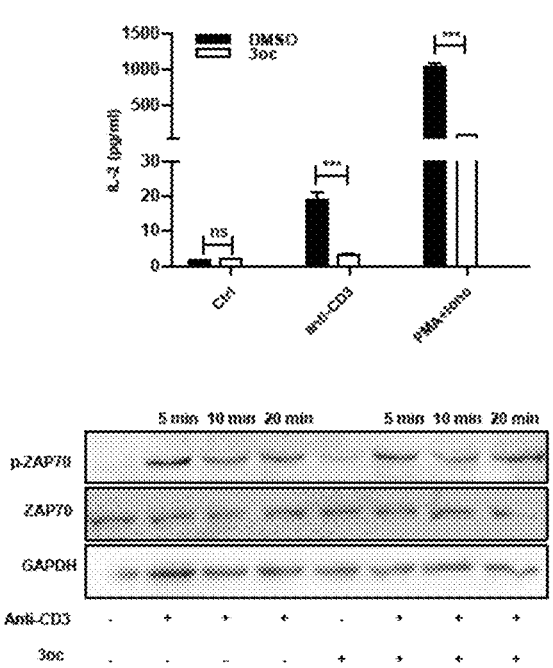
Figure 1:
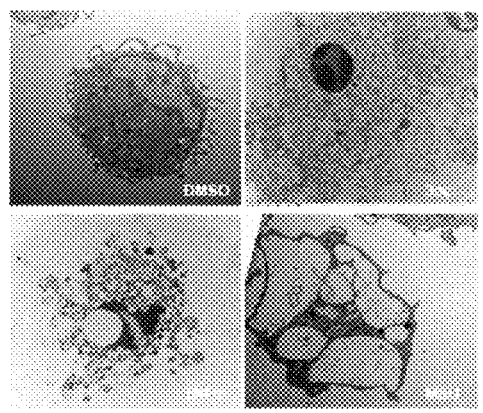

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

In addition, terms such as "first" and "second" are used herein for purposes of description and are not intended to indicate or imply relative importance or significance.

Use of a TNFR1-FADD-Caspase8-Caspase3 Pathway Inhibitor

According to embodiments of a first broad aspect of the present disclosure, there is provided use of a TNFR1-FADD-caspase8-caspase3 pathway inhibitor in preparation of a medicament for treating an immune system related disease caused by autoinducer.

Wherein TNFR1-FADD-caspase8-caspase3 pathway is that upon TNFR1 activation, FADD is recruited to the inner cell membrane and is associated with the intracellular domain of TNFR1. FADD in turn is associated with Caspase-8 and the latter is activated. The activated Caspase-8 then cleaves the pro-Caspase-3 to produce mature Caspase-3 for downstream apoptotic cell death. According to the embodiments, autoinducer, such as 3OC12 HSL, can activate immune cell TNFR1-FADD-caspase8-caspase3 pathway and then induce immune cell apoptosis and cause immune system related disease. Furthermore, the inventor discovered that TNFR1-FADD-caspase8-caspase3 pathway inhibitor showed significant therapeutic effect in treating immune system related disease caused by autoinducer.

According to an embodiments of present disclosure, the autoinducer is derived from *Pseudomonas aeruginosa*. *Pseudomonas aeruginosa* (PA) is a pathogen responsible to severe opportunistic. In PA, LasR-LasI QS circuit uses N-(3-oxo-dodecanoyl) homoserine lactone (3OC12 HSL or 3OC) as the autoinducer that represents a large family of autoinducers differing mainly at the length of acyl chain. According to the embodiments, the inventor discovered that *Pseudomonas aeruginosa* (PA) results in a forced expulsion of TNF receptor 1 (TNFR1) into the disordered phase of membrane. The displaced TNFR1 demonstrates higher motion speeds and extended migratory trajectories on live cell membrane, leading to a higher degree of spontaneous trimerization and TNFR1 signaling without external ligand. This distribution shift drives the entire process of caspase 8-caspase 3 axis activation and apoptotic cell death. It was found that TNFR1-FADD-caspase8-caspase3 pathway inhibitor showed more significant therapeutic effect in treating immune system related disease caused by autoinducer derived from *Pseudomonas aeruginosa* and *Pseudomonas aeruginosa* infection-related disease.

According to some embodiments of present disclosure, the TNFR1-FADD-caspase8-caspase3 pathway inhibitor is at least one selected from a group consisting of a TNFR1 inhibitor, a TNFR1 trimerization inhibitor, a FADD inhibitor, a caspase inhibitor.

According to one embodiment of present disclosure, the TNFR1 trimerization inhibitor comprises: (a) a competitive inhibitor peptide for TNFR1, such as TNFR-like T2; or (b) a nucleic acid or construct expressing (a). Wherein competitive inhibitor peptide for TNFR1 is that a synthetic or recombinant polypeptide that can interfere with TNFα binding to TNFR1 that reduces TNFR-1 ligand-induced trimerization. It was also found that competitive inhibitor peptide for TNFR1 or nucleic acid or construct expressing the peptide was an effective TNFR1 trimerization inhibitor. The competitive inhibitor peptide for TNFR1 or nucleic acid or construct expressing the peptide showed significant therapeutic effect in treating immune system related disease caused by autoinducer.

According to one embodiment of present disclosure, the TNFR1 inhibitor comprises at least one selected from a group consisting of a TNFR1 expression inhibitor, a TNFR1 mutant inducer, a TNFR1 functional inhibitor, a TNFR1 functional analog. Wherein TNFR1 expression inhibitor is the agent for inhibiting TNFR1 expression, which include but not limited to NFKb pathway inhibitor. Wherein TNFR1 mutant inducer is the agent for inducing TNFR1 loss of function mutation, which include but not limited to the agent for inducing TNFR1 Palmitoylation. Wherein TNFR1 functional inhibitor is the agent for inhibit TNFR1 activating, which include but not limited to the antibody specific to TNFR1. Wherein TNFR1 functional analog is the competitive antagonist of TNFR1. The TNFR1 inhibitor showed above can inhibit TNFR1 expression or inhibit TNFR1 activating and then prevent apoptosis caused by autoinducer effectively.

According to another embodiment of present disclosure, the FADD inhibitor comprises at least one selected from a group consisting of a FADD expression inhibitor, a FADD mutant inducer, a FADD functional inhibitor, a FADD functional analog. Wherein FADD expression inhibitor is the agent for inhibiting FADD expression. Wherein FADD mutant inducer is the agent for inducing FADD loss of function mutation. Wherein FADD functional inhibitor is the agent for inhibit FADD activating, which include but not limited to expression of dominant negative FADD and NSC 47147 (small molecule inhibitor). Wherein FADD functional analog is the competitive antagonist of FADD. The FADD inhibitor showed above can inhibit FADD expression or inhibit FADD activating and then prevent apoptosis caused by autoinducer effectively.

According to another embodiments of present disclosure, the caspase inhibitor comprises at least one selected from a group consisting of Z-VAD, Z-DEVD, Z-IETD, Emricasan, a shRNA specific to caspase, an agent inducing deviating away from caspase pathway by activating RIP1. Wherein deviating away from caspase pathway by activating RIP1 is that depending on the cell type, RIP1 activation can lead to cell signaling related to NFkb and MAPK signaling that activate the treated cells, rather than apoptotic signaling conventionally associated with cell death. The caspase inhibitor showed above can inhibit caspase expression or inhibit caspase activating and then prevent apoptosis caused by autoinducer effectively.

According to embodiments of present disclosure, the autoinducer is $C_{8\sim12}$ alkyl acyl homoserine lactone or derivatives thereof. Through experiments, it's found that $C_{8\sim12}$, especially $C_{12}$ alkyl acyl homoserine lactone or derivatives thereof can induce immune cell apoptosis and cause immune system related disease seriously. TNFR1-FADD-caspase8-caspase3 pathway inhibitor showed significant therapeutic effect in treating immune system related disease caused by $C_{8\sim12}$, especially $C_8$ alkyl acyl homoserine lactone or derivatives thereof.

Also, according to embodiments of another broad aspect of the present disclosure, there is provided use of a method for treating an immune system related disease caused by autoinducer, comprising: administrating a TNFR1-FADD-caspase8-caspase3 pathway inhibitor to a subject in need thereof. As described above, autoinducer, such as 3OC12 HSL, can activate immune cell TNFR1-FADD-caspase8-caspase3 pathway and then induce immune cell apoptosis and cause immune system related disease. Furthermore, the inventor also discovered that administrating a TNFR1-FADD-caspase8-caspase3 pathway inhibitor to a subject in need thereof showed significant therapeutic effect in treating immune system related disease caused by autoinducer.

Wherein the autoinducer, the immune system related disease and the TNFR1-FADD-caspase8-caspase3 pathway inhibitor is as mentioned above.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "treat", "treating" or "treatment" of any disease or disorder refers to all processes wherein there may be a slowing, interrupting, arresting, controlling, or stopping of the progression of the disease or disorder, but does not necessarily indicate a total elimination of all the disorder symptoms, as well as the prophylactic therapy of the mentioned conditions, particularly in a patient who is predisposed to such disease or disorder. In some embodiments, "treat", "treating" or "treatment" refers to ameliorating the disease or disorder (i.e., slowing or arresting or reducing the development of the disease or at least one of the clinical symptoms thereof). In other embodiments, "treat", "treating" or "treatment" refers to alleviating or ameliorating at least one physical parameter including those which may not be discernible by the patient. In other embodiments, "treat", "treating" or "treatment" refers to modulating the disease or disorder, either physically, (e.g., stabilization of a discernible symptom), physiologically, (e.g., stabilization of a physical parameter), or both. In other embodiment, "treat", "treating" or "treatment" refers to preventing or delaying the onset or development or progression of the disease or disorder.

As used herein, the term "therapeutically effective amount" or "therapeutically effective dosage" refers to the amount of the compound of the invention which is capable of eliciting biological or medical response (Such as reducing or inhibiting the activity of an enzyme or protein, or ameliorating symptoms, alleviating symptoms, slowing or delaying the development of the disease, or preventing diseases, etc.) of an individual. In one non-limiting embodiment, the term "therapeutically effective amount" refers to, when the compound of the present invention is administered to a subject. In other embodiment, the term "therapeutically effective amount" refers to, when administering the cell, or organ, or non-cellular biological material, or medium, an effective amount of the compounds of the present invention, which can at least partially reduce or inhibit TNFR1-FADD-caspase8-caspase3 pathway activation; or at least partially reduce or inhibit the TNFR1 trimerization.

As used herein, the terms "administration of" and "administering a" compound should be understood to mean providing a compound of the inhibitor or a prodrug of a compound of the invention to an individual in need thereof. It is recognized that one skilled in the art can treat a patient presently afflicted with immune system related disease with an effective amount of the compound of the inhibitor.

The term "composition" as used herein is intended to encompass a product comprising the specified ingredients in the specified amounts, as well as any product which results, directly or indirectly, from combinations of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from a combination, complexation or aggregation of any two or more of the ingredients, or from the dissociation of one or more of the ingredients, or from the other types of reactions or interactions of one or more of the ingredients. Accordingly, the pharmaceutical compositions of the present invention encompass any composition made by mixing a compound and a pharmaceutically acceptable carrier.

Method for Screening a Medicament

According to embodiments of another broad aspect of the present disclosure, there is provided a method for screening a medicament for treating an immune system related disease caused by autoinducer, comprising: (1) contacting a candidate compound with an immune cell; (2) determining at least one of the following prior to and after the contacting: (a) a trimerization level of a cell surface TNFR1; (b) an activation level of a TNFR1-FADD-caspase8-caspase3 pathway, wherein the decrease of the trimerization level of a cell surface TNFR1 or the decrease of the activation level of a TNFR1-FADD-caspase8-caspase3 pathway is an indication for the candidate compound is a medicament for treating an immune system related disease caused by autoinducer. According to the embodiments, the method described above can screen a medicament for treating an immune system related disease caused by autoinducer effectively.

According to the embodiments of present disclosure, the autoinducer is $C_{8-12}$ alkyl acyl homoserine lactone or derivatives thereof. Through experiments, it's found that $C_{8-12}$, especially $C_8$ alkyl acyl homoserine lactone or derivatives thereof can significantly induce TNFR1 trimerization and activate TNFR1-FADD-caspase8-caspase3 pathway. The results under the method for screening a medicament for treating an immune system related disease caused by autoinducer, especially by $C_{8-12}$, especially $C_8$ alkyl acyl homoserine lactone or derivatives thereof are more reliable. The method is more sensitive.

Compounds or Pharmaceutical Composition

The present invention also provides a pharmaceutical composition comprising compounds screening under the method described above. According to the specific examples of the present invention, the pharmaceutical composition can further comprise pharmaceutically acceptable excipient, carrier, adjuvant, solvent and a combination thereof.

The present invention provides a method of treating, preventing or ameliorating a disease or disorder, comprising administrating a safe and effective amount of a combination of drugs containing compounds and one or more therapeutic active agents. Among them, the combination of drugs comprises one or more additional drugs for treatment of immune system related disease caused by autoinducer, especially *Pseudomonas aeruginosa* infection-related disease.

Other drugs for treatment of immune system related disease caused by autoinducer, especially *Pseudomonas aeruginosa* infection-related disease include, are not limited to: aminoglycosides (gentamicin, amikacin, and tobramycin), quinolones (ciprofloxacin and levofloxacin), and cephalosporins (ceftazidime, cefepime, cefoperazone, cefpirome, and ceftobiprole).

The amount of the compound of the pharmaceutical composition disclosed herein refers to an amount which can be effectively inhibit TNFR1-FADD-caspase8-caspase3 pathway or TNFR1 trimerization. The dosage of active ingredient in the compositions of this invention may be varied, however, it is necessary that the amount of the active ingredient be such that a suitable dosage form is obtained. The active ingredient may be administered to patients (animals or human) in need of such treatment in dosage that will provide optimal pharmaceutical efficacy. The selected dosage upon the desired therapeutic effect, on the route of administration, and on the duration of the treatment. The dosage will vary from patient to patient depending upon the nature and severity of disease, the patient's weight, special diet then being followed by a patient, concurrent medication, and other factors which those skilled in the art will recognize. The dosage range will generally be about 0.5 mg to 1.0 g per patient per day which may be administered in single or multiple doses. In one embodiment, the dosage range will be about 0.5 mg to 500 mg per patient per day; in anther embodiment about 0.5 mg to 200 mg per patient per day; and in yet another embodiment about 5 mg to 50 mg per patient per day.

It will also be appreciated that certain of the compounds of the present invention can exist in free form for treatment, or where appropriate, as a pharmaceutically acceptable derivative or a prodrug thereof. A pharmaceutically acceptable derivative includes pharmaceutically acceptable salts, esters, salts of such esters, or any other adduct or derivative which upon administration to a patient in need thereof is capable of providing, directly or indirectly, a compound as otherwise described herein, or a metabolite or residue thereof.

The pharmaceutical compositions of the invention may be prepared and packaged in bulk form wherein a safe and effective amount of a compound of Formula (I) disclosed herein can be extracted and then given to the patient, such as with powders or syrups. Generally, dosage levels of between 0.0001 to 10 mg/kg of body weight daily are administered to the patient to obtain effective antagonism of TNFR1 receptors or TNFR1-FADD-caspase8-caspase3 pathway. The pharmaceutical compositions of the invention may be prepared and packaged in unit dosage form wherein each physically discrete unit contains a safe and effective amount of a compound of Formula (I) disclosed herein. When prepared in unit dosage form, the pharmaceutical compositions of the invention commonly contain from about 0.5 mg to 1 g, or 1 mg to 700 mg, or 5 mg to 100 mg, of the compound.

When the pharmaceutical compositions of the present invention also contain one or more other active ingredients, in addition to a compound of the present invention, the weight ratio of the compound of the present invention to the second active ingredient may be varied and depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to 1:200. Combinations of a compound of the present invention and other active ingredients will generally also be within the aforementioned range, but in each case, an effective dose of each active ingredient should be used.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition. The pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared at for example environment temperature and under barometric pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

In one embodiment, the compounds disclosed herein can be prepared to oral. In the other embodiment, the compounds disclosed herein can be prepared to inhalation. In the still other embodiment, the compounds disclosed herein can be prepared to nasal administration. In the yet other embodiment, the compounds disclosed herein can be prepared to transdermal administration. In the still yet other embodiments, the compounds disclosed herein can be prepared to topical administration.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Miccellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, polyepsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80 and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In other aspect, the pharmaceutical composition of the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (e.g. micronised) compound can be defined by a $D_{50}$ value of about 1 to about 10 microns (for example as measured using laser diffraction).

Aerosols may be formed by suspending or dissolving a compound disclosed herein or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as *arachis* oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

In one embodiment, the therapies disclosed herein comprise administrating a safe and effective amount of the compound or the pharmaceutical composition containing the compound to patients in need. Each example disclosed herein comprises the method of treating the diseases above comprising administrating a safe and effective amount of the compound of the inhibitor or the pharmaceutical composition containing the compound of the inhibitor to patients in need.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In a further embodiment, the compound of the invention or the pharmaceutical composition thereof may be administered intranasally.

In one embodiment, the compound of the invention or the pharmaceutical composition thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as absorption, distribution, and half-life, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally or parenterally, advantageously intravenously, e.g., as a suspension or in aqueous solution.

In one embodiment, a therapeutically effective dosage of the compound disclosed herein from about 0.1 mg to about 2,000 mg per day. The pharmaceutical compositions should provide a dosage of from about 0.1 mg to about 2000 mg of the compound. In a special embodiment, pharmaceutical dosage unit forms are prepared to provide from about 1 mg to about 2,000 mg, about 10 mg to about 1,000 mg, about 20 mg to about 500 mg, or about 25 mg to about 250 mg of the active ingredient or a combination of essential ingredients per dosage unit form. In a special embodiment, pharmaceutical dosage unit forms are prepared to provide about 10 mg, 20 mg, 25 mg, 50 mg, 100 mg, 250 mg, 500 mg, 1000 mg or 2000 mg of the active ingredient.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The following examples are provided so that the invention might be more fully understood. However, it should be understood that these embodiments merely provide a method of practicing the present invention, and the present invention is not limited to these embodiments.

The related methods are described as follows:

Mice, Cells and Reagents

C57BL/6, OT-I and OT-II mice were obtained from Jackson laboratories. These and Casp8−/−, Ripk3−/− and Tnfrsf1a−/− mice were bred and housed per approved protocols in at Tsinghua University Animal Facilities.

N-3-oxo-dodecanoyl-(3OC12 HSL), N-dodecanoyl-(C12 HSL), N-butyryl-(C4 HSL), Nhexanoyl-(C6 HSL), N-octanoyl-(C8 HSL), N-3-oxo-octanoyl-(3OC8 HSL), N-decanoyl-(C10 HSL), N-trtradecanoyl-(C14 HSL), N-hexadecanoyl-L-homoserine lactone (C6 HSL) were from Cayman Chemical; Egg sphingomyelin (860061), 1,2-dioleoyl-sn-glycero-3-phosphocholine (DOPC) (850375), 1,2-dipalmitoyl-sn-glycero-3-phosphocholine (DPPC) (850355) and cholesterol were from Avanti Polar Lipids; Annexin V-FITC/PI apoptosis detection Kit (no. FXP018-100) was from 4A Biotech Co. OT-I peptide (aa257-264) and OT-II peptide (aa323-339) were synthesized by Beijing SciLight Biotechnology; PMA and Ionomycin mixture (no. CS1001) was from Multi Sciences Biotech; Recombinant human TNF α (no. 300-01A) was purchased from PeproTech; cycloheximide (no. C7698) was from Sigma; lipofectamine 2000 (no. 11668019) and DTSSP (no. 21578), Quantum dot 605streptavidin conjugates (no. Q10103MP) were from ThermoFisher; Caspase inhibitors were from Enzo life sciences; Protein A+G agarose (no. P2012) and ONPG (no. ST429) were from Beyotime Biothchnology; mouse CD4+ T cell pre-enrichment kit (no. 19772) was from StemCell; Elisa detection kits for mouse IL-1β (88-7013-88), mouse TNF α (88-7324-88) and mouse IL-2 (no. 88-7024-88) were from eBiosciences.

For Western blots, Iκbα (no. 9242), caspase-3 (8G10, no. 9665), caspase 8 (D35G2, no. 4790), cleaved caspase 8 (Asp387, no. 9429), TNFR1 (C25C1, no. 3736), EGFR (2232), pEGFR (4407) were from CST; GAPDH (AG019) was from Beyotime Biotechnology; TNFR1 (50496-RP02) was from Sino Biological; Fas (A-20, sc-1023) was from Santa Cruz. For immunoprecipitation, FADD (H-181, sc-5559) and caspase 8 p18 (C-20, sc-6136) were from Santa Cruz. For flow cytometry, anti-mouse CD69-FITC (no. 11-0691), anti-mouse CD4-PE (no. 12-0041), anti-mouse CD8a-PE (no. 12-0081) were from eBiosciences. For single particle tracking, anti-mouse TNFR1 (PA1-40282) was from Thermo Scientific, and anti-BSA moue Ab was from Sigma.

pcDNA3.1(+), pcDNA3.1-N-FLAG, peGFP-N1 were gifts from Dr. Li Yu of Tsinghua University; human EGFR-peGFP-N1 was a gift from Dr Xiaohong Fang of the Institute of Chemistry, Chinese Academy of Sciences; human TNFR1 cDNA clone (HG10872-M) was purchased from Sino Biological; human TNFR1 (1-293) mutant was amplified from human TNFR1 with specific primers and cloned into peGFP-N1 vector; huFADD-DN cDNA was amplified from Jurkat cDNA library with specific primers and cloned into pcDNA3.1-N-flag; human FcγRIIA cDNA was amplified from THP-1 cDNA library and cloned into peGFP-N1. All plasmids were verified by sequencing. QS molecule bioassay strain Agrobacterium tumefaciens (JZA1) 1 and wild type strain (PAO1) and LasI-deficient (ΔLasI) and LasR-deficient (ΔLasR) mutants 2 were as previously described.

HEK 293, RAW264.7, DC2.4, THP-1, EL-4, A20 cells were grown in DMEM (HyClone) supplemented with 10% FBS, 100 U/ml penicillin and 100 mg/ml streptomycin. Cos-1 cells were from Cell Resource Center, IBMS, CAMS/PUMC; HELA cells were a gift from Dr. Xiaohong Fang in Institute of Chemistry, Chinese Academy of Science, H9 cells were obtained from China Center for Type Culture Collection. All these cells were grown in the same culture media plus 10 mM HEPES and 50 μM β-mercaptoethanol.

Cell Assays

Cell apoptosis was detected with Annexin V/PI apoptosis detection Kit. Briefly, cells were stimulated with HSLs or left untreated. 6 hrs later, cells were collected and stained with Annexin VFITC and PI for 15 min at RT, then the apoptotic effect was measured by flow cytometry. OT-I or OT-II splenocytes were pulsed with specific peptides or PMA and ionomycin mixture with or without HSLs or TNF α plus cycloheximide. 24 hrs later, cells and supernatants were collected separately. For OT-I activation, cells were stained with CD69 and CD8. For OT-II activation, cells were stained with CD69 and CD4. Cell activation was measured by flow cytometry. All supernatants were detected for IL-2 secretion by ELISA.

For bone marrow cell-PA co-culture assay, bone marrow cells were isolated from C57BL/6 mice and inoculated with the supernatant of WT, LasI or LasR-deficient PA cultures for 6 hrs. Samples were stained with LY6G and the number of neutrophil was counted by flow cytometry.

Co-Immunoprecipitation, Cross-Linking, Lipid Raft Isolation and Western Blot

For FADD immunoprecipitation, 4 μg anti-mouse FADD pAb (Santa Cruz, H-181) were incubated with 100 μl protein A/G agarose for 2 hrs at RT. 3 million/ml purified CD4 T cells were stimulated with HSLs or left untreated. The cells were then collected and lysed with IP lysis buffer (50 mM HEPES pH 7.4, 150 mM NaCl, 1% NP-40, 1 mM EDTA, 1 mM PMSF, 1 mM NaF, 1 mM NaVO3 and protease inhibitor cocktails). The cell lysates were added into antibody-bead mixtures for 3 hrs at 4° C. Beads were then collected by low speed centrifugation (1000 g, 5 min) and washed 4 times with IP lysis buffer (300 mM NaCl added). After the last wash, pellets were suspended with 70 ul 2×SDS loading buffer and boiled for 5 min. For caspase 8 immunoprecipitation, 4 μg anti-Caspase 8 pAb (Santa Cruz, C-20) was incubated with 100 μl protein A/G agarose for 1 hr at RT. 3 million/ml H9 cells were treated with HSLs or left untreated. The samples were processed as in FADD IP. For cross-linking assay, CD4+ T cells isolated from C57BL/6 mice spleen or human THP-1 cells was stimulated with HSLs or left untreated, then cells were collected and cross-linked by 10 mM DTSSP at RT for 30 min and quenched with 1M Tris-HCl (pH7.5) for 15 min. The cells were then lysed with RIPA buffer from Bytotime biotechnology (50 mM Tris (pH 7.4), 150 mM NaCl, 1% Triton X-100, 1% sodium deoxycholate, 0.1% SDS, 1 mM EDTA, 1 mM PMSF, 1 mM NaF, 1 mM NaVO3 and protease inhibitor cocktails) and mixed with non-reducing SDS loading buffer. Lipid rafts were isolated as described before 3. Briefly, THP-1 cells were lysed on ice for 20 min in 1 ml of 1% Triton X-100 in MN buffer (25 mM 2-(N-morpholino) ethanesulfonic acid, 150 mM NaCl; pH 6.5). The cell lysate was homogenized with a loose-fitting Dounce homogenizer (10 strokes) and then was spun at 500 g for 7 min at 4° C.; The postnuclear supernatant was centrifuged first at 7000 g for 12 min and then at 100,000 g for 50 min, at 4° C. The pellets were resuspended in 200-octylglucopyranoside buffer and are referred to as DIG fractions. All samples were mixed with 3×SDS loading buffer and boiled for 5 min before Western blotting analysis.

Quorum Sensing Molecule Distribution Assay

JZA1 system was modified from the wild type as described previously 1. For this assay JZA1 was first pre-induced. Briefly, JZA1 was grown in LB liquid medium containing 1 μg/ml tetracycline, 100 μg/ml spectinomycin and 100 μg/ml gentamycin at 28° C. until the late-log phase. 1 ml of the culture was added into 100 ml AT medium containing antibiotics at 28° C. until it entered the mid-log phase. Bacteria were then collected by centrifuging (12000 g, 10 min) and resuspended in 15% sterilized glycerol for freezing. To perform the membrane retention assay, H9 cells were incubated with HSLs at 37° C. Then the cells and supernatants were collected separately by centrifuging (1500 rpm, 5 min). The cells were treated with Buffer #1 (20 mM Tris-HCl, 2 mM EDTA, 1 mM DTT, 10% glycerol) on ice to break membrane. Cytosol and membrane fragments were separated by ultra-centrifuging (179000 g, 24 min, 4° C.). The membrane fragments were dissolved in Buffer #2 (Buffer #1 with 1% Triton-X100). HSLs in the fractions were extracted with ethyl acetate and air dried at RT. The samples were then dissolved in DMSO and cultured with 2 μl pre-induced JZA1 strain in 2 ml AT medium at 28° C. for 20 hrs. As OD 600 nm reached 0.2-1, the bacteria were lysed by mixing 200 μl cell culture with 200 μl Z buffer 4, 10 μl 0.05% SDS and 15 μl chloroform. 100 μl ONPG (4 mg/ml) was added into each sample and the time T0 was recorded. The reactions were terminated by adding 600 μl 1M NaCO3 and the time Ts recorded. Their OD 420 nm was measured to determine the Miller unit.

Lipid Binding Assay 1 mg/ml of each lipid species in chloroform was coated on round glass slides by evaporation.

Then the glass slices were incubated with 100 μM 3OC12 HSL in DMSO in PBS at 37° C. After the incubation, the glass slices were washed slightly with PBS for 4-5 times and lipids were dissolved with DMSO. The amount of 3OC12 HSL in each sample was measured by QS bioassay as described above.

Single Molecule Fluorescence Imaging

Optical setup: Single-molecule fluorescence detection was performed on a home-built objective type total internal reflection fluorescence microscope (TIRFM) based on an inverted Zeiss Observer-A 1 stand. Briefly, a laser combiner that contains 4 single-wavelength CW lasers (405, 488, 561, and 640 nm) (Coherent) was used as the excitation light source. The excitation light was introduced to the excitation path via a polarization-preserved single-mode optical fiber and a reflective collimator. The light was first gated by an acousto-optic turnable filter (AOTF), then expended by 5 times with a pair of lenses, and lastly focused on the back focal plan of an Olympus TIRF objective (100×, NA 1.49) with a lens (f=150 mm) that can be translated perpendicular to the optical axis to achieve variable incident angle. The fluorescence signal is collected by the same objective and then filtered and spectrally separated with Optosplit II (Cairn Research) before being projected to an electron-multiplying charge coupled device (EMCCD) camera (Andor iXon DU-897U BV). The data acquisition is controlled by Micro-Manager that drives the AOTF and the EMCCD camera.

Single molecule photo-bleaching step counting: 0.5 μg TNFR1(1-293)-peGFP-N1 plasmid or 0.5 μg EGFR-peGFP-N1 plasmid was transfected into HeLa cells and cultured for 5-6 hrs. Then the cells were stimulated with HSLs, TNF α, or left untreated, and washed twice with PBS and fixed with 4% paraformaldehyde before imaging. GFP was excited at 488 nm with a laser power of 5 mW measured after the laser passing through the objective. The collected fluorescent signal was gated by a band-pass filter HQ 525/50 (Chroma Technology). The EM gain of the EMCCD camera was set at 300. Movies of 400 frames were acquired for each sample at a full-frame rate of 10 Hz. For imaging analysis, the background fluorescence was firstly subtracted from the movie acquired from the fixed cells using the rolling ball method in Image J software, and regions of interest on movies were selected manually according to the outline of cells. To analyze the bleaching steps, the fluorescence time courses of each fluorescent spots were first constructed by Image J plugin and bleaching steps were then counted manually.

Quantum Dot-Based Single Particle Tracking

To track individual TNFR1 on the cell membrane, anti-TNFR1 IgG (was first papain digested to yield a Fab fragment. The Fab was then conjugated with biotin through the unique —SH at its C terminal. To prepare anti TNFR1 Fab QD conjugates, a solution of 0.7 nM anti TNFR1—Fab-biotin in 1 ml of DMEM was added drop-wise to 1 ml of 2 nM QD 605-streptavidin conjugate. Cell monolayers (50% confluent) previously serum starved for 1 hr were treated with 3OC12 HSL or left untreated and incubated with 500 ml of the final anti TNFR1-Fab-QD solution at 25° C. for 2 min. The cells were then washed twice with PBS at 25° C., placed in serum-free medium, and loaded for imaging. For single-FcγIIA tracking, Fc fragment was obtained by papain digestion of an anti-BSA IgG (Sigma Aldrich). Fc-QD conjugate was produced as described before. Cos-1 cells were transiently transfected with Fcγ RIIA plasmid, 24 hrs later, cells were stimulated with 3OC12 HSL or left untreated and incubated with 500 ml of the final Fc-QD solution at 25° C. for 2 min. Quantum dot-labeled cells were imaged in TIRF mode. The fluorescence was excited at 488 nm and gated by a band-pass filter (575-640, Carl Zeiss). The excitation power was about 2 mW measured after the objective. Movies of 400 frames were acquired for each sample at a full-frame rate of 17 Hz. Individual trajectories were constructed by Utrack written in Matlab. Diffusion coefficient and plot area were calculated by customized programs written with Matlab. For motion pattern determination by MSD-t analysis 5: linear, simple Brownian diffusion; open-up parabolic, directed diffusion; open-down parabolic, restricted diffusion; and near zero, stationary.

PA Lung Infection 6-8 week old C57BL/6 mice were infected intratracheally (i.t.) with 2×106 or 1×107 CFU of PAO1, ΔLasI and ΔLasR PA under mild anesthesia. 24 hrs later, lungs of infected mice were excised and homogenized for bacteria number calculation. Supernatants were collected by low-speed centrifuging were assayed for cytokines. Neutrophil numbers were detected by flow cytometry from lung tissue suspension.

Bone Marrow Chimaeras 5 week old C57BL/6 mice were γ-irradiated with a dose of 5.5 Gy twice and 3 hrs later bone marrow cells were cross-transplanted by i.v route (WT to WT, Casp8−/−Ripk3−/− to WT, Tnfrsf1a−/− to WT). Mice were kept on antibiotics (Neomycin 1 mg/ml and Polymycin 0.1 mg/ml) for 3 weeks. Infection with 1×107 CFU of PAO1 bacteria was performed 6 weeks post-reconstitution. For CD45.1/CD45.2 chimera transplantation, 5 week old C57BL/6 mice were γ irradiated with 5.5 Gy twice and 3 hrs later bone marrow cells (CD45.1:CD45.2=1:1) were mixed and cross-transplanted by i.v route. After 4 weeks, mice were infected with 1×107 CFU of P.A bacteria as described before.

Phagocytosis Assay

For Phagocytic assay, polystyrene beads were coated with BSA plus mouse anti-BSA Ab via commercial methods. Before experiment, RAW264.7 cells were cultured on clean glass slices in 24-hole plate with Opti-MEM. Cells were co-cultured with coated beads, centrifuged at 900 g, 4° C. for 5 min and cultured at 37° C. for 45 min. Then cells were fixed with 4% paraformaldehyde and stained with 488 nm anti-mouse fluorescent Ab for immunofluorescent imaging. For analysis, total number of beads on each cell was calculated under bright field, the number of beads which were not engulfed were calculated under fluorescent lighting.

Atomic Force Microscopy

For lipid small unilamellar vesicles (SUV) production, chloroform solution of lipids (DOPC:DPPC=1:1, DOPC:SM:chol=3:6:1) in chloroform were mixed in glass vials and dried under a stream of nitrogen gas. The dried lipid film was resuspended with 4 mM HEPES buffer (with 150 mM NaCl) to produce SUV. Vesicle solution (100 µl) was added to freshly cleaved mica clamped in a fluid cell on the AFM heater head. After incubation at 55° C. for 30 min and then kept at RT for another 30 min, the bilayers were rinsed extensively with HEPES buffer to remove excess vesicles.

AFM images were obtained at RT on a NanoScope V Multimode Scanning Probe Microscope (Digital Instrument, Veeco, Santa Barbara, Calif., USA) in the tapping mode using V shape Si3N4 tips (model DNL-10) with spring constants of ~0.35 N/m and resonance frequencies between 8 and 10 kHz in aqueous solutions. All experiments were conducted in Hepes buffer using a commercially available fluid cell, sealed by an O-ring. A J scanner (125 µm×125 µm) was used with a scan rate between 0.8 and 2 Hz per line.

Transmission Electron Microscopy

For TEM analyses, cultured cells were processed in situ for fixation, dehydration, infiltration and embedding in culture dish. The cells were prefixed with 2.5% glutaraldehyde in 0.1 M phosphate buffer, pH 7.2 for 2 hrs and post fixed with cacodylate buffered 1% osmium tetroxide for 1 hr at RT. Cells were then dehydrated through graded ethanol and embedded in Epon mixture. After polymerizing, the hardened Epon layer containing the embedded cells was separated from the plastic culture dish. Under a light microscope a representative area was selected, trimmed and glued to resin stub for sectioning. Ultra-thin sections were cut with a diamond knife on an ultramicrotome (EM UC6, Leica) and collected on single hole grids with copper supporting film. The sections were stained with aqueous uranyl acetate and Reynolds's lead citrate and observed under a Hitachi H7650 TEM at 80 kV. The images were acquired with a Morada G2 (Olympus) digital camera mounted on the microscope. Samples for SEM imaging were prepared and fixed using 2.5% glutaraldehyde solution followed by ethanol and HMDS gradient dehydration or critical point drying. Samples were sputter coated with gold (JEC-3000FC, JEOL). Samples were then inspected under an Electron Microscope (JSM-700F, JEOL).

Statistics

For all assays, a minimum of 5 mice were used in each condition and all experiments were repeated at least three times. All plot graphs show means with SEM. Statistical analysis for each independent experiment was performed with an unpaired, Student's t test. A p value of less than 0.05 was considered significant. *: <0.05; : <0.01; *: <0.001; N.S.: not significant.

EXAMPLES

Figure 2A:
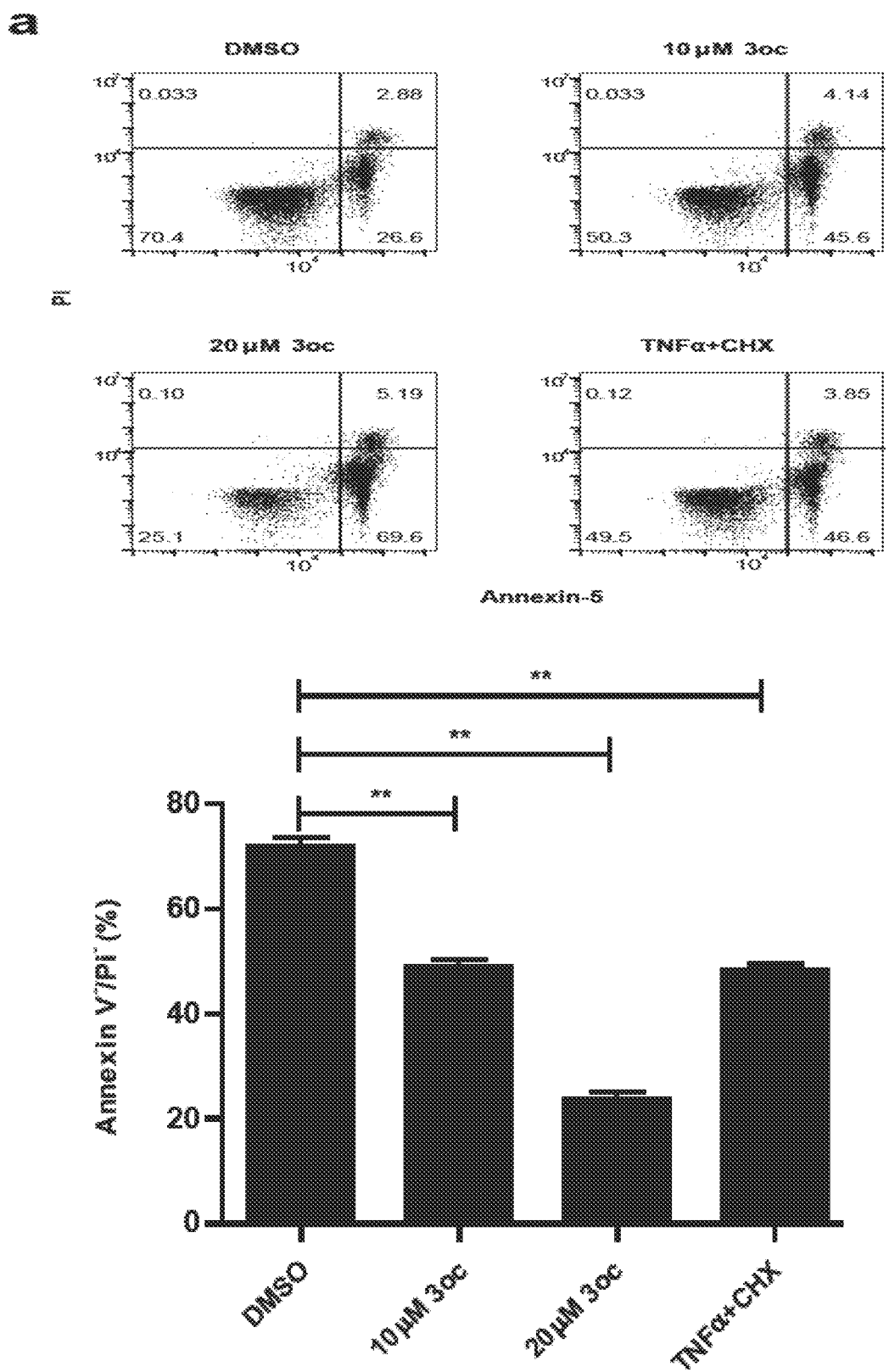
FIG. 2 shows 3OC12 HSL induces extrinsic apoptosis on mammalian cells.
Figure 2B:
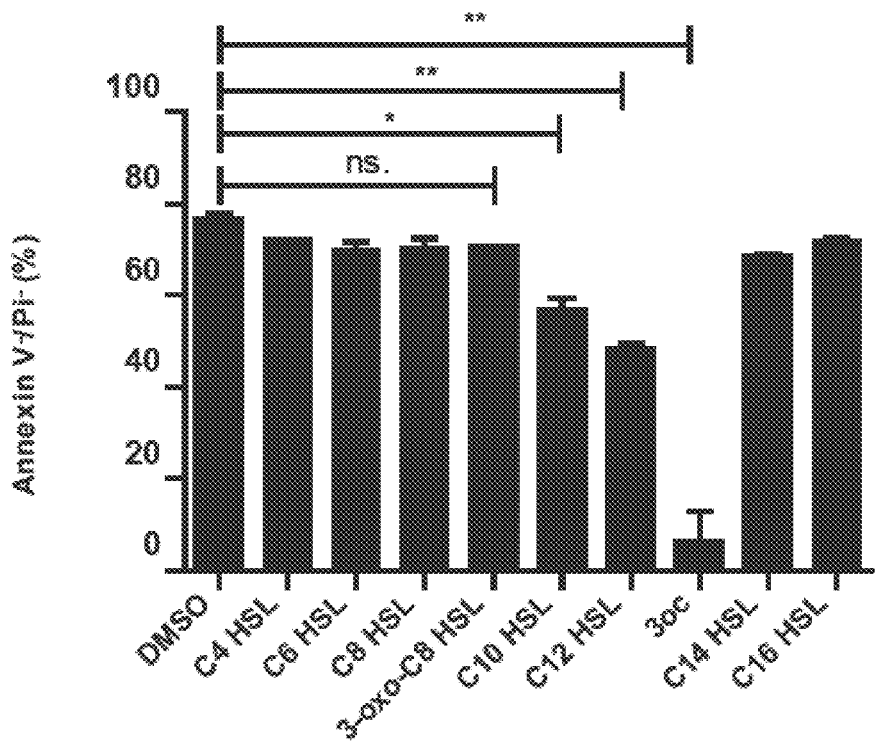

To search for the signaling pathways in mammalian cells, inventors first confirmed the previous reports that 3OC12 HSL can suppress primary T cell and T cell line activation induced by cognate MHC class I and class II-restricted antigens or PMA plus ionophore, as measured by IL-2 release and CD69 expression (FIGS. 1a and b). In the live cells recovered from the culture, ZAP70 phosphorylation was minimally affected, suggesting that TCR-originated signal was not significantly affected in surviving cells (FIG. 1c). However, at modest concentrations of 10 and 20 µM, 3OC12 HSL triggered significant T cell death, similar to the standard protocol of cycloheximide plus TNFα (FIG. 2a). Therefore the immune-suppressive effect can be at least partially explained as a consequence of cell loss. We therefore elected to initiate the search of signaling mechanisms from its role in cell death induction. Among the analogs of 3OC12 HSL, apoptosis was induced by those with acyl chains of 10 and 12 carbons (FIG. 2b). FIG. 1c shows that most immune cell types including thymoma line EL4, transformed DC line DC2.4, reticuloma A20, monocytic RAW264.7, and leukemia line THP-1 were sensitive to 3OC12 HSL; human lymphoblast H9 and thioglycolate-induced macrophages were relatively resistant.

Figure 2C:
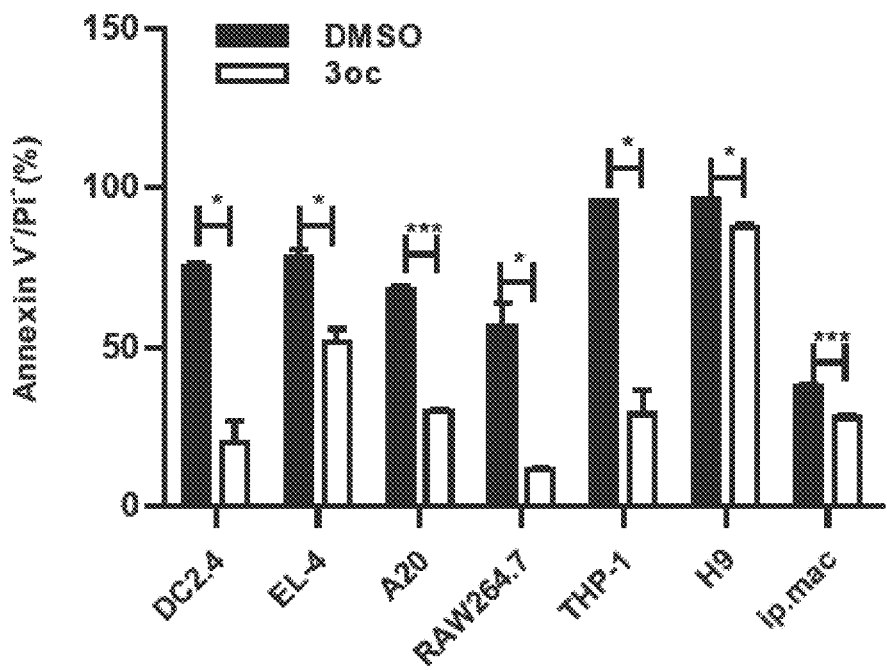

Extended data FIG. 2c shows that 3OC12 HSL-treated cells displayed typical apoptotic membrane ruffling and nuclear condensation, in contrast with the cytoplasmic swelling in monosodium urate crystal-treated cells. Among many cellular effects reported, 3OC12 HSL also triggers caspase 8 activation although no attempts have been made to establish the mechanism.

Figure 2D:
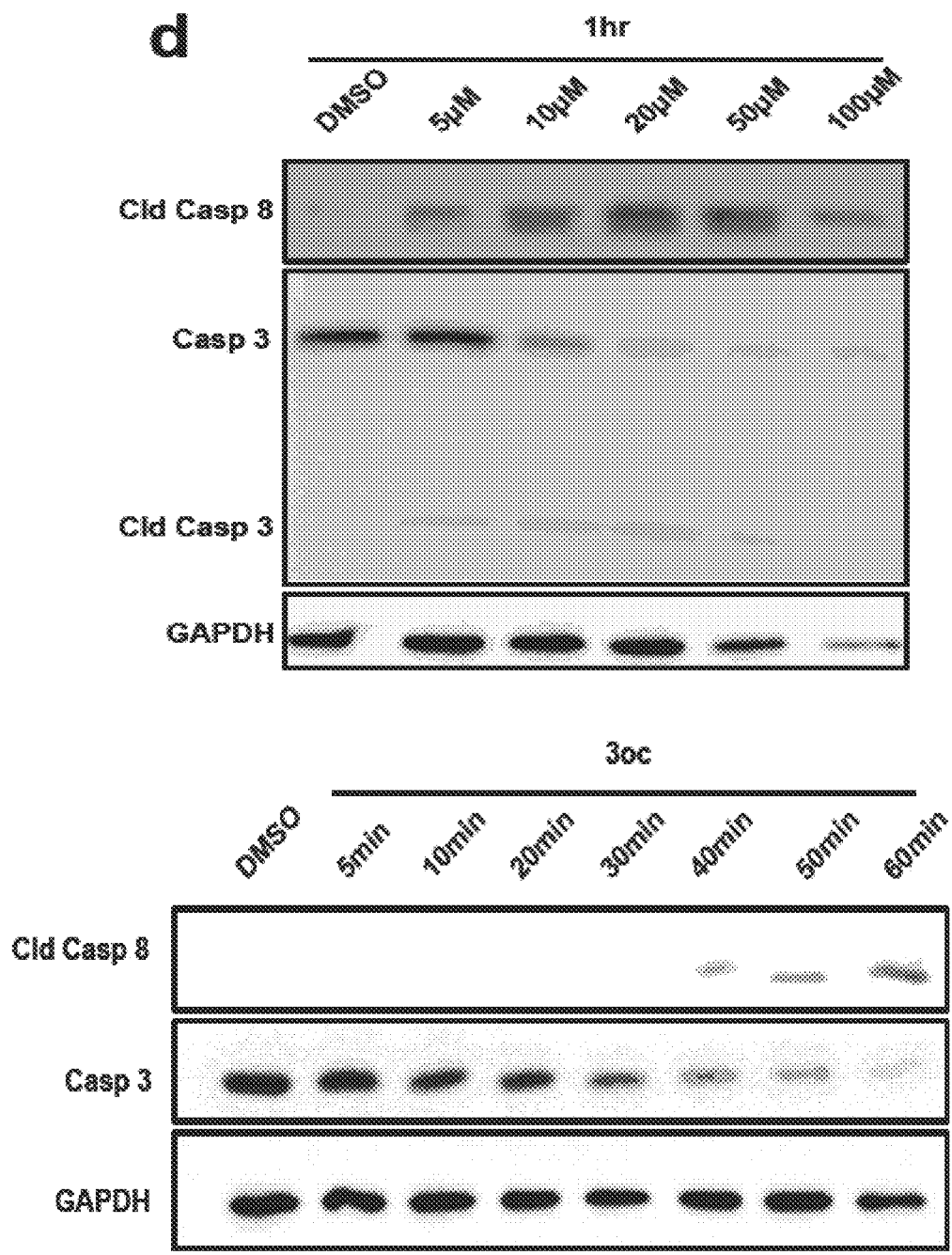
Figure 2E:
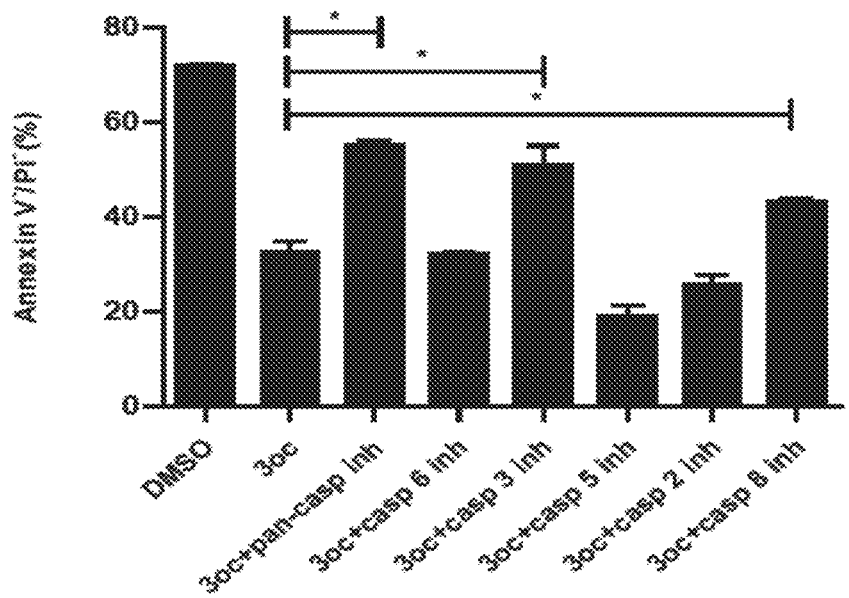
Figure 2F:
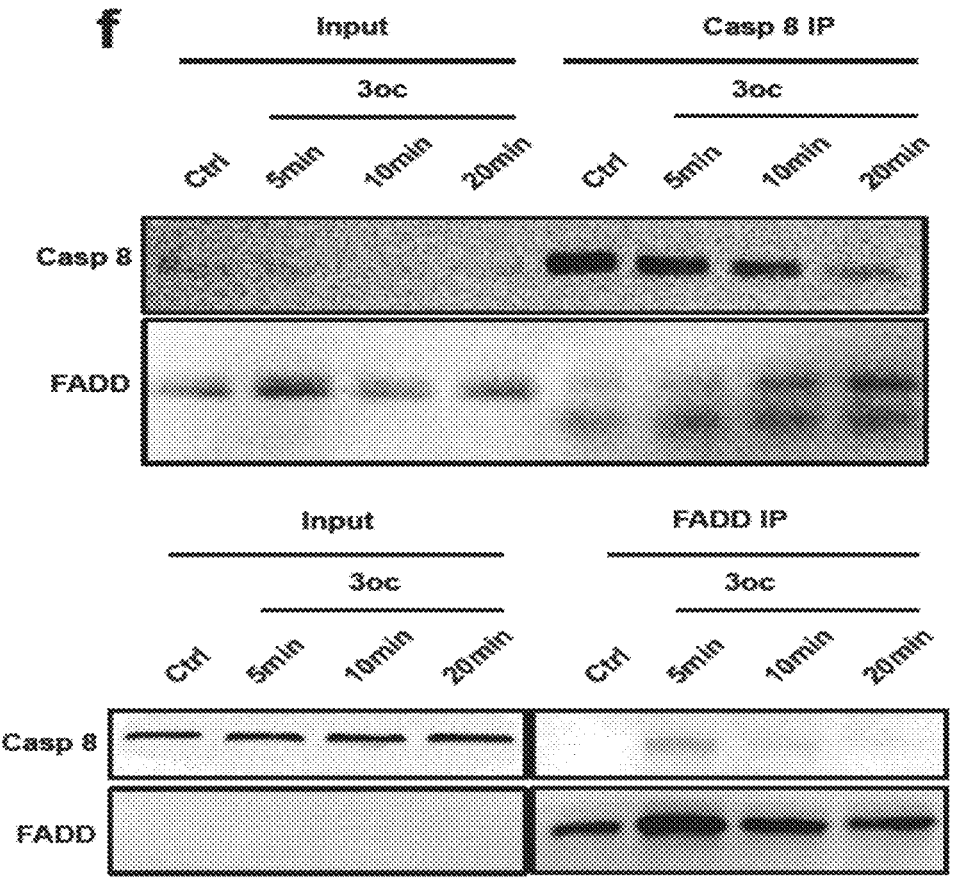
Figure 3:
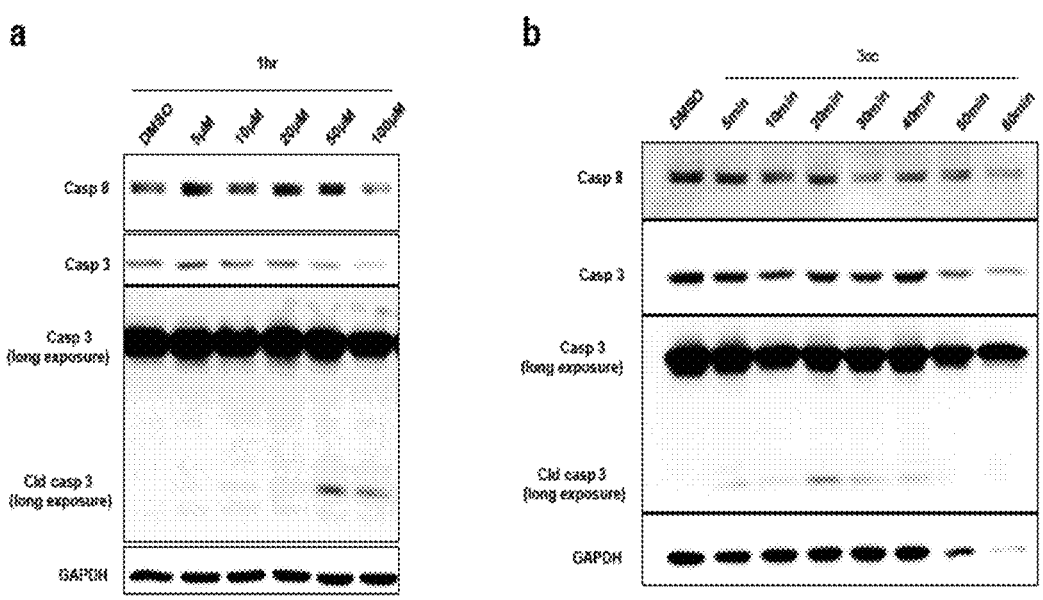
FIG. 3 shows 3OC12 HSL induces caspase 8 and caspase 3 cleavage in human cells.
Figure 4:
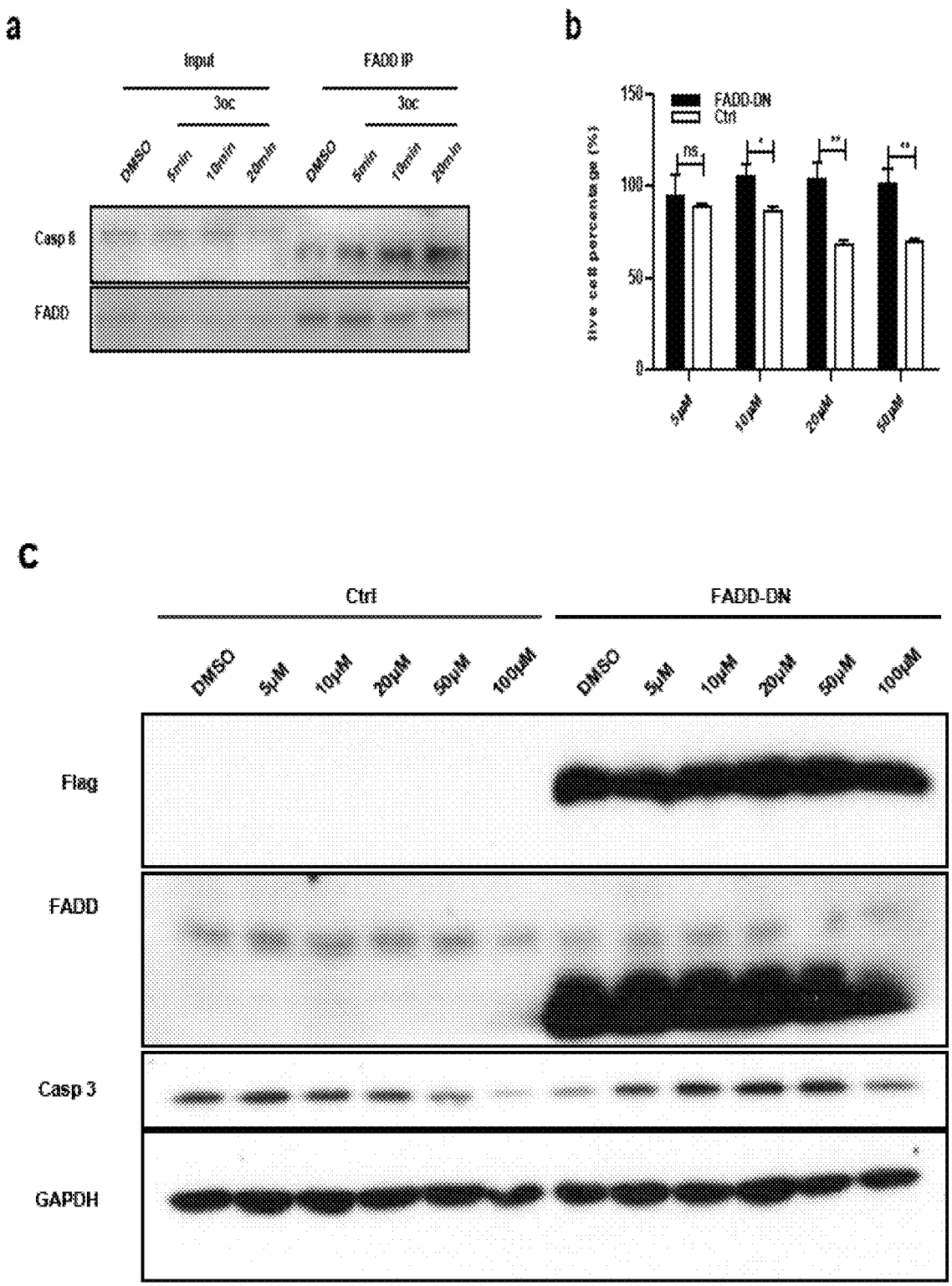
FIG. 4 shows FADD is essential for 3OC12 HSL-induced apoptosis.

In 3OC12 HSL-treated CD4 T cells, caspases 8 and 3 were cleaved in a dose and time-dependent manner (FIG. 2d mouse, and FIGS. 3a and b, human). Among caspase inhibitors, only pan-caspase inhibitor Z-VAD, caspase 3 inhibitor Z-DEVD, and caspase 8 inhibitor Z-IETD reduced the cytotoxicity in comparison with the 3OC12 HSL treatment along (FIG. 2e), suggesting that the cell death was downstream of the caspase 8/3 pathway. In immunoprecipitation assays, FADD (Fas-associated protein with death domain) was found to be in complex with caspase 8 following the treatment, and the association became stronger as caspase 8 being digested (FIG. 2f and FIG. 4a). A dominant negative version of FADD also reduced 3OC12 HSL-induced cell death (FIG. 4b) and caspase 3 cleavage (FIG. 4c), suggesting that in the presence of 3OC12 HSL, the trigger of apoptosis was originated from the plasma membrane.

Figure 2G:
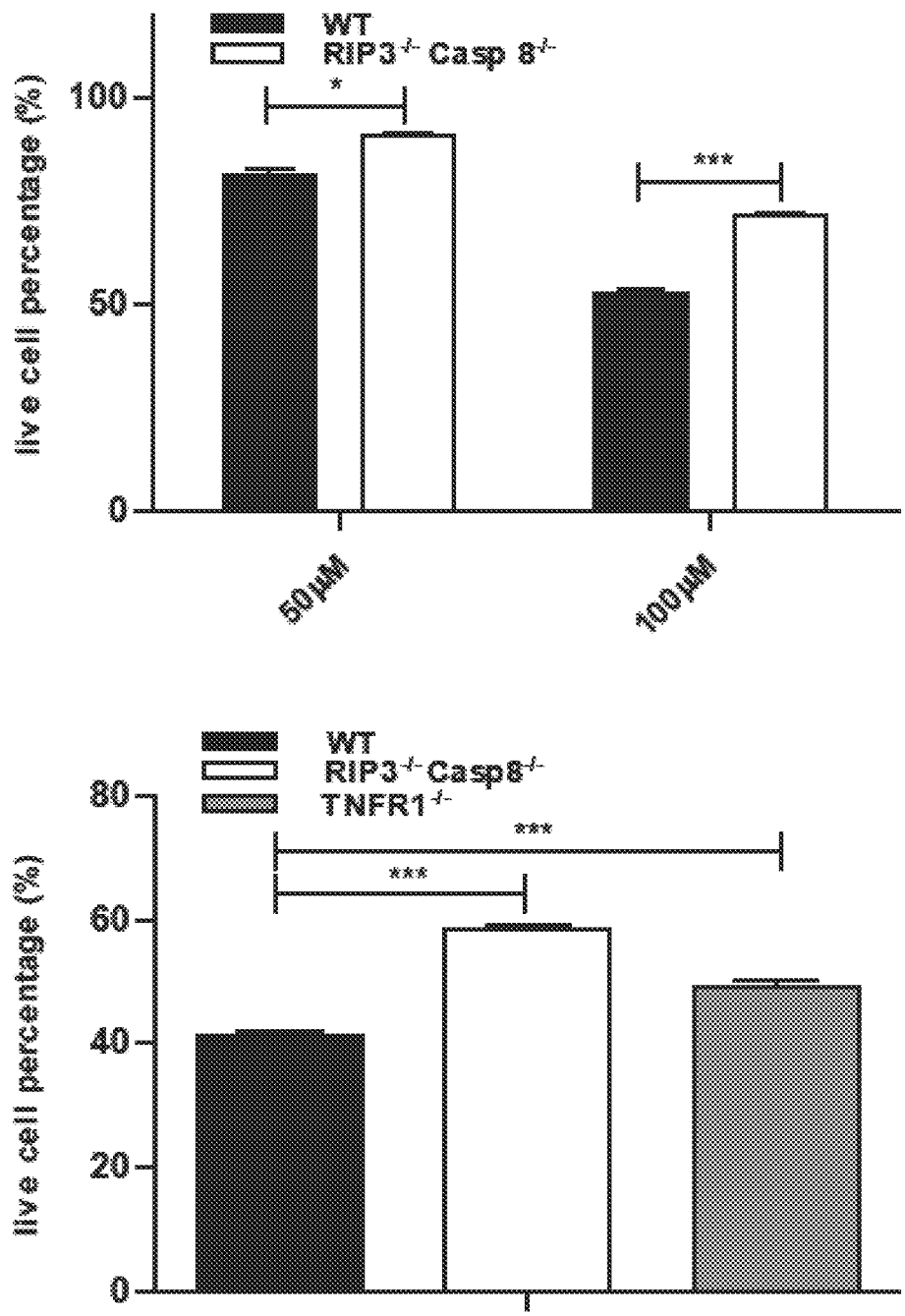
Figure 5:
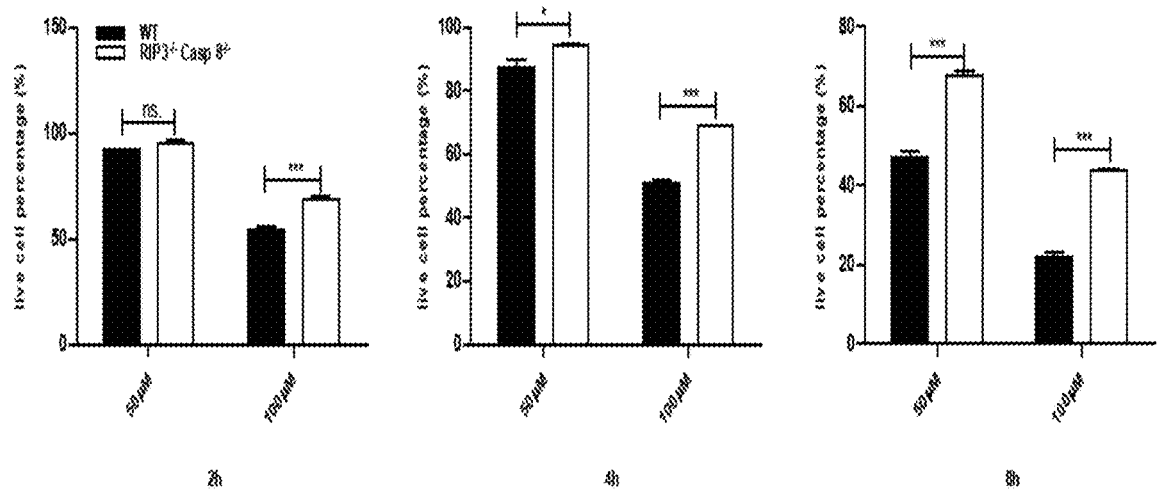
FIG. 5 shows Caspase 8 or TNFR1 deficiency partially rescues 3OC12 HSL induced apoptosis.
Figure 5:
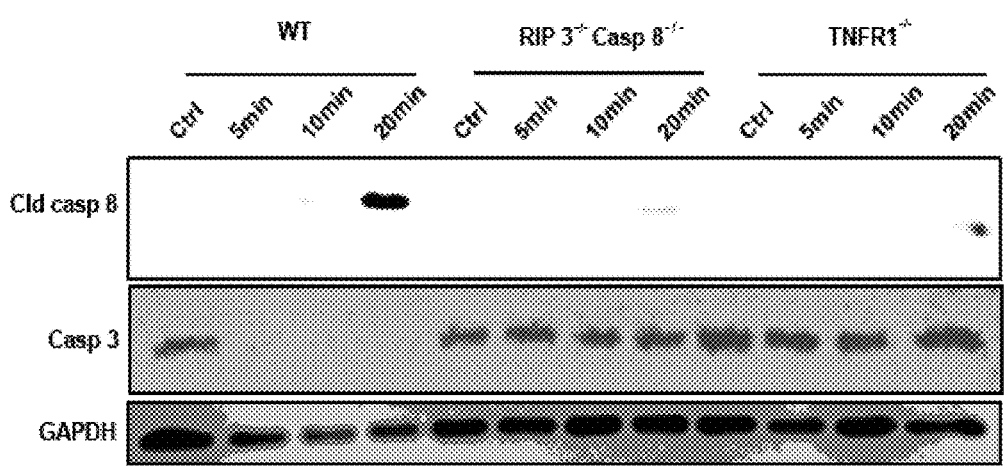
Figure 6:
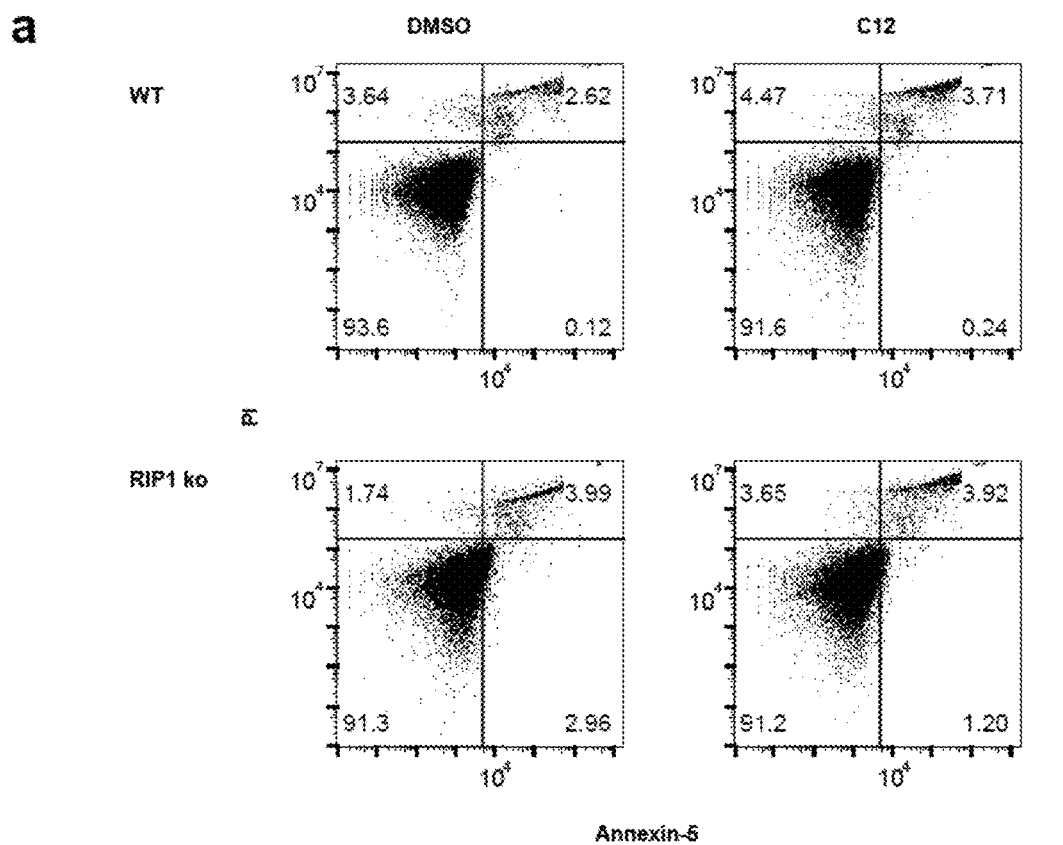
FIG. 6 shows 3OC12 HSL causes NF κb activation in apoptosis-resistant cells.
Figure 6:
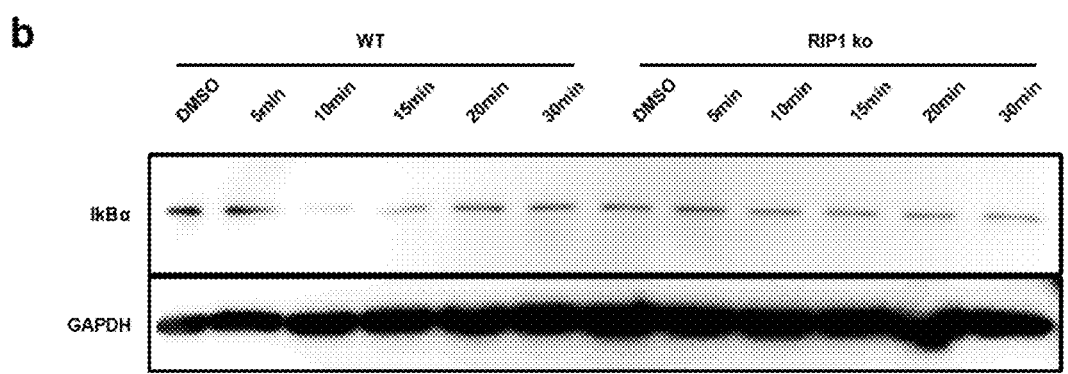

Upstream of caspase 8, pleotropic TNFR family members mediate both pro-survival NF κb activation and apoptotic programming. Indeed, Casp8−/− Ripk3−/− macrophages were more resistant to 3OC12 HSL-mediated cell death, a phenotype shared by and Tnfrsf1a−/− splenocytes (FIG. 2g) with the difference becoming more evident from 2 to 8 hrs (FIG. 5a). The weaker signaling in these mutants was confirmed by the reduced caspase 3 cleavage in TNFR1 and caspase 8 mutants (FIG. 5b). The inventor found that in 3OC12 HSL-treated non-apoptotic Jurkat cells, Iκbα was degraded. In a Ripk1−/− version of the same cell line, IκbΑ remained intact in comparison (FIGS. 6a and b). These results suggest that 3OC12 HSL activates a surface structure that signals via FADD, and depending on the cell type, transmits signals via either RIP1 for NF κb activation or caspase 8 for apoptosis. This is the typical behavior of TNFR family members upon ligand binding, which was clearly absent in the inventor's setting.

Figure 7A:
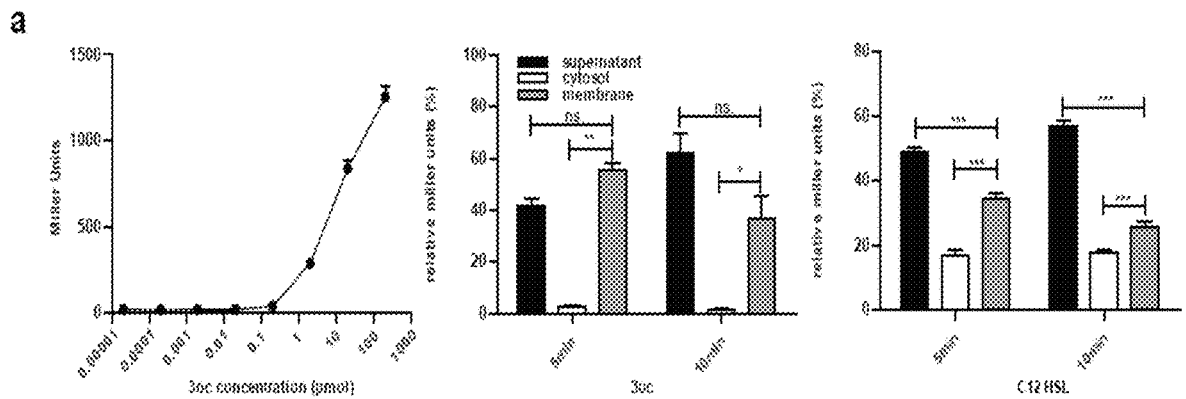
FIG. 7 shows 3OC12 HSL is enriched in the plasma membrane.
Figure 7B:
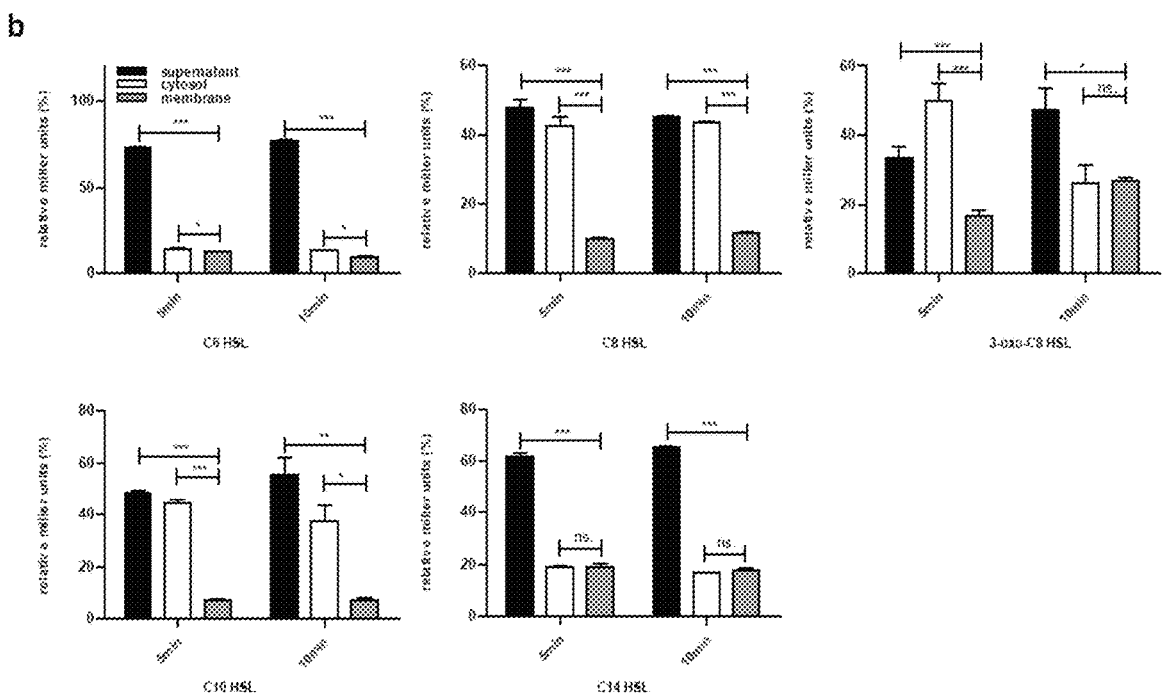
Figure 7C:
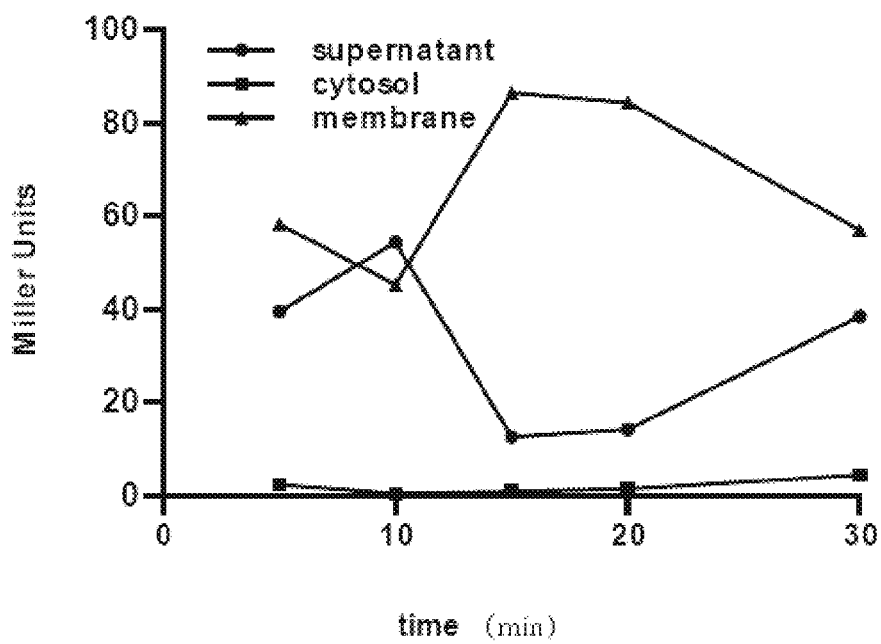
Figure 7D:
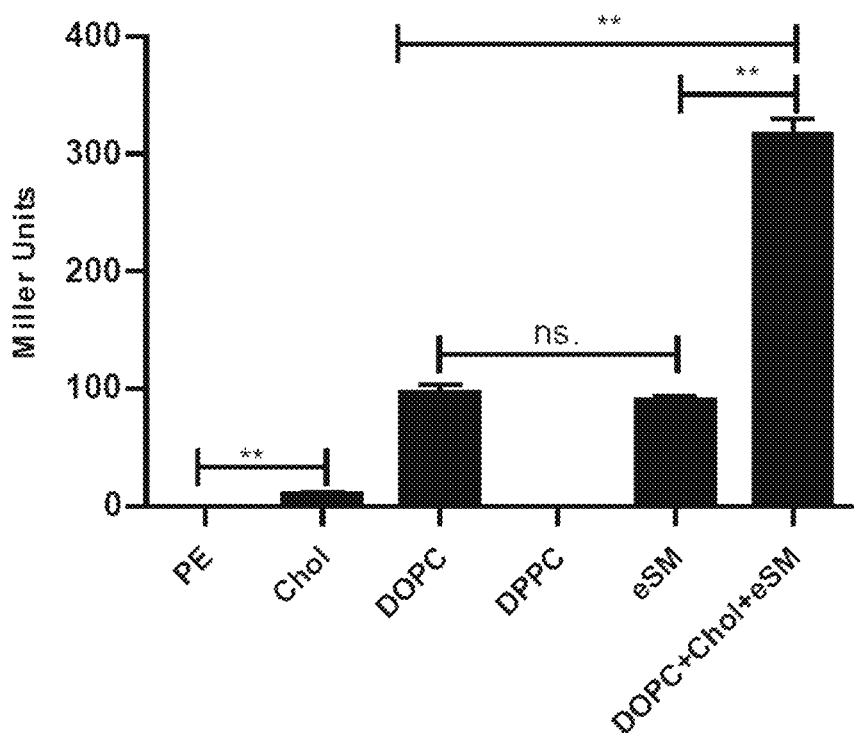
Figure 7E:
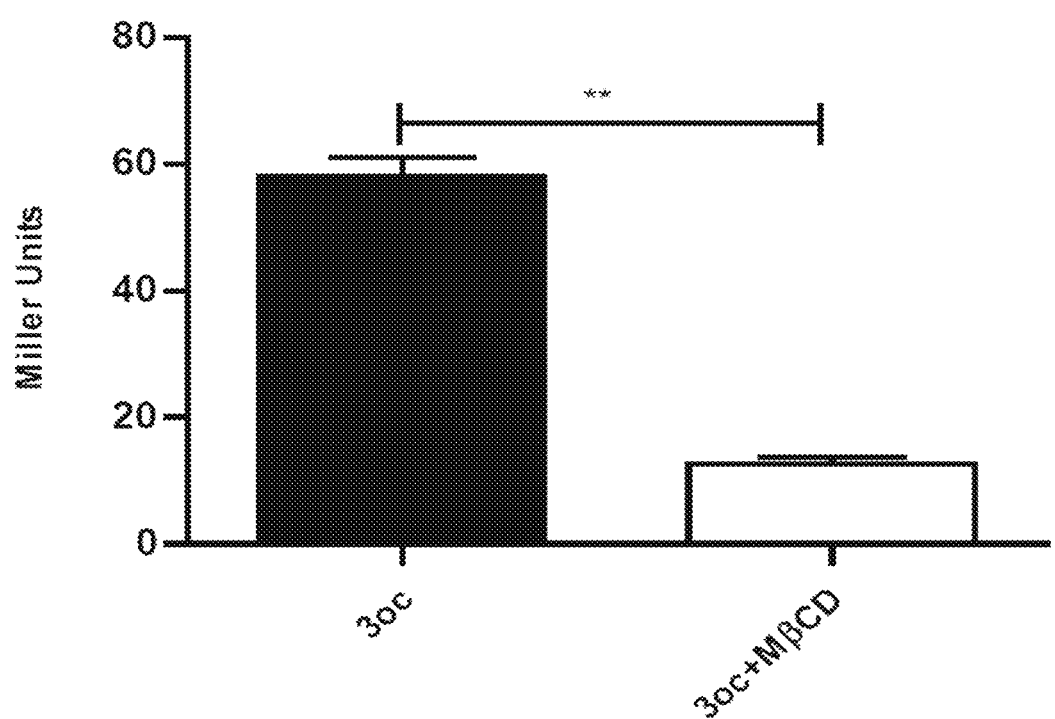

The inventors wondered if the increased hydrophobicity is associated with their ability to be retained in the plasma membrane. 3OC12 HSL was added to the mildly apoptosis-resistant H9 cell culture (FIG. 7a), and the plasma membrane was extracted using differential centrifugation. Analogs with acyl chains from 6 to 14 carbons were used as controls. A refined ultra-sensitive system for autoinducer detection based on β-galactosidase reporter was used for quantification (FIG. 7a). Measured by percentage of Miller units detected in each fraction from the same starting cell numbers, 3OC12 HSL and C12 HSL were found to be in higher amounts in the plasma membrane fraction, with a smaller presence in the cytoplasm (FIG. 7a). In comparison, this membrane enrichment was not as evident for C6, C8, 3-oxo-C8, C10 and C14 analogs (FIG. 7b). For 3OC12 HSL, this distribution pattern was persistent over time (FIG. 7c). In bacterial membrane, HSL-based autoinducers are freely diffusible through the external enclosure 20. To identify eukaryotic membrane components necessary for 3OC12 HSL's retention, dioleoyl (DOPC) and dipalmitoyl (DPPC) phosphatidylcholine, phosphatidylethanolamine (PE), cholesterol and sphingomyelin individually or in combination in chloroform were coated onto glass disks and air-dried. The disks were then covered by a 3OC12 HSL solution. After washing, the corresponding disks were eluted with DMSO. FIG. 7d shows that only lipid components containing cholesterol, sphingomyelin and DOPC were able to efficiently retain 3OC12 HSL. Furthermore, in H9 cells treated with MβCD to remove cholesterol therefore disrupting ordered lipid domains, the retention was significantly reduced (FIG. 7e). This result indicates that HSL retention in the membrane is dependent on both side chain length and lipid domains, and this membrane entrapment effect echoes the side chain lengths required for apoptosis induction (FIG. 2b).

Figure 8A:
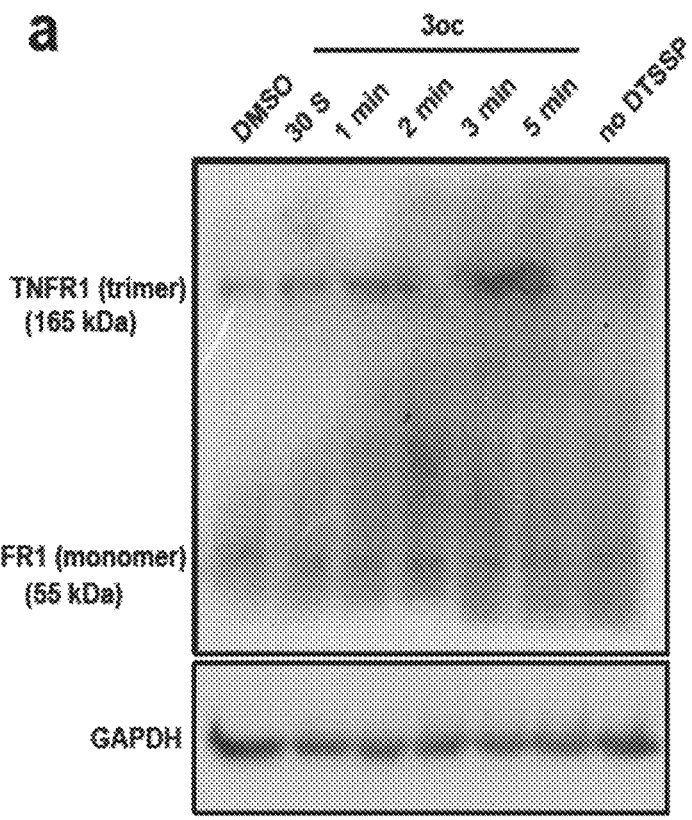
FIG. 8 shows 3OC12 HSL disrupts the structure of plasma membrane and induces TNFR1 autotrimerization.
Figure 9:
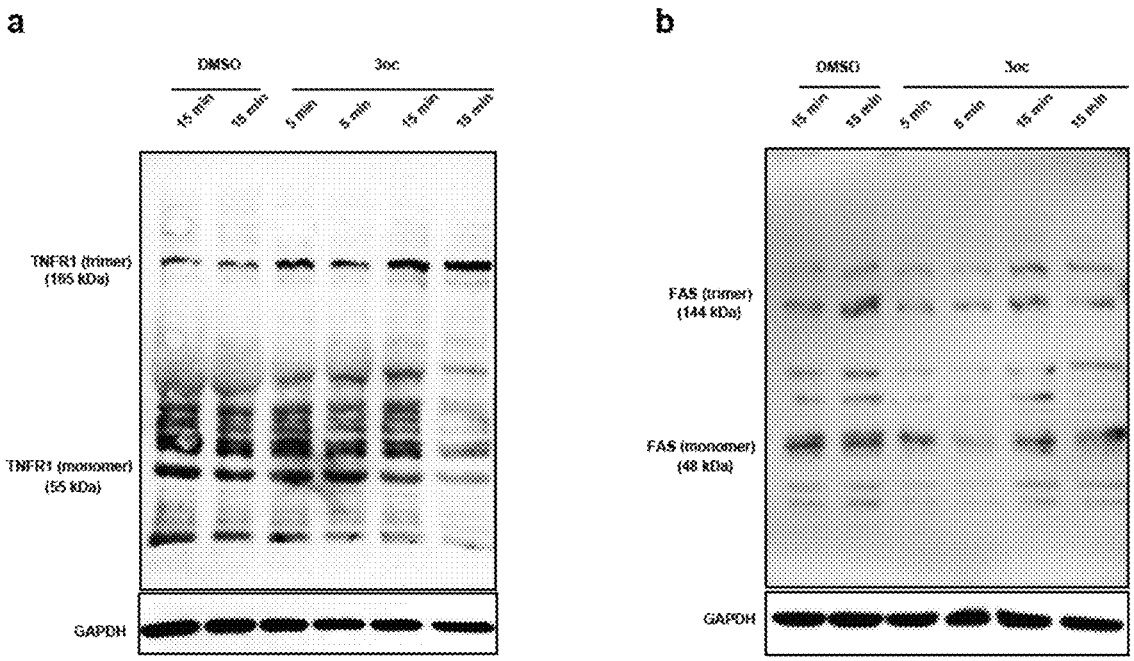
FIG. 9 shows 3OC12 HSL promotes TNFR1 but not FAS trimerization.

In death-inducing signaling complex (DISC), FADD is an adaptor that bridges cytoplasmic tails of TNFR family members and cytosolic caspase 8. This signaling cascade becomes active upon the trimerization of these receptors. It is generally believed that TNFR1 moves out of the ordered lipid domains upon ligand binding, emanating apoptotic signal thereafter, in a diametric contrast with Fas which moves into lipid ordered domains following FasL binding. The inventors first studied whether the presence of 3OC12 HSL changed the oligomerization of TNFR1 and Fas. With a crosslinker DTSSP and run under non-reducing condition, 3OC12 HSL rapidly increased the amount of a band with approximate 3 times the molecular weight of TNFR1 monomer (FIG. 8a and FIG. 9a). Fas however did not show a significant change, even after a prolonged incubation (FIG. 9b). The baseline TNFR1 trimerization is consistent with previous reports that a fraction of this receptor undergoes spontaneous aggregation induced by its extracellular trimerization domain.

Figure 8B:
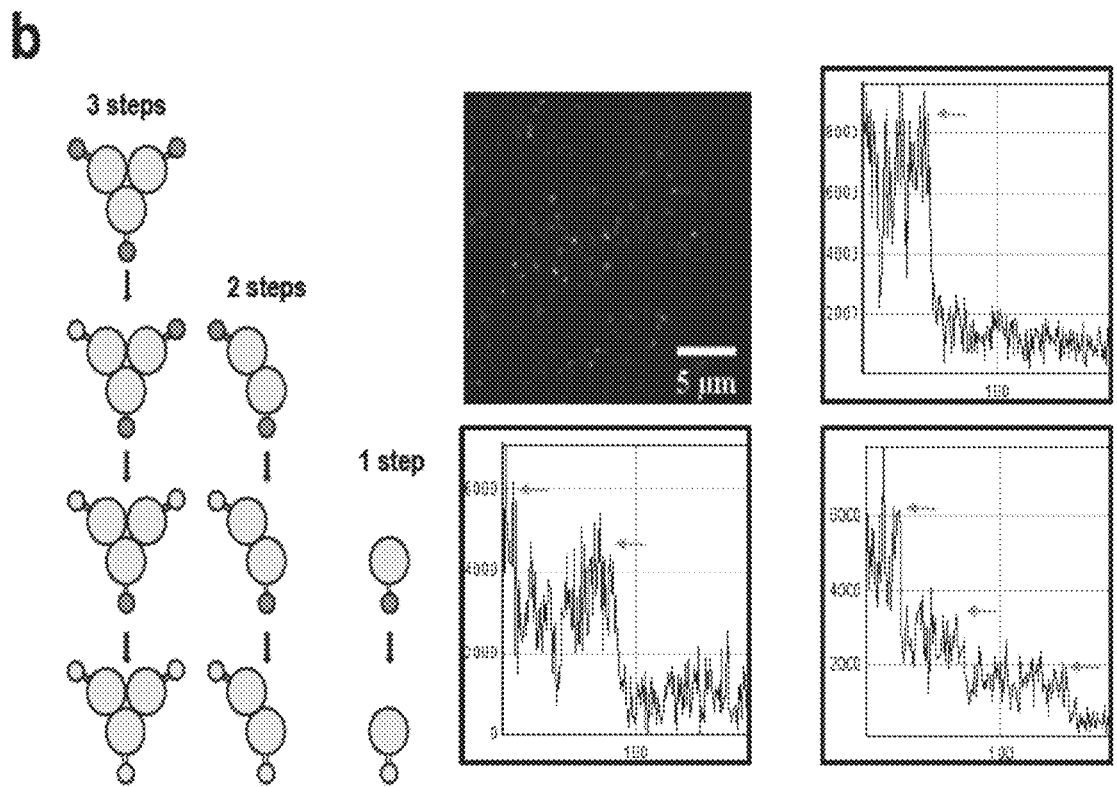
Figure 8C:
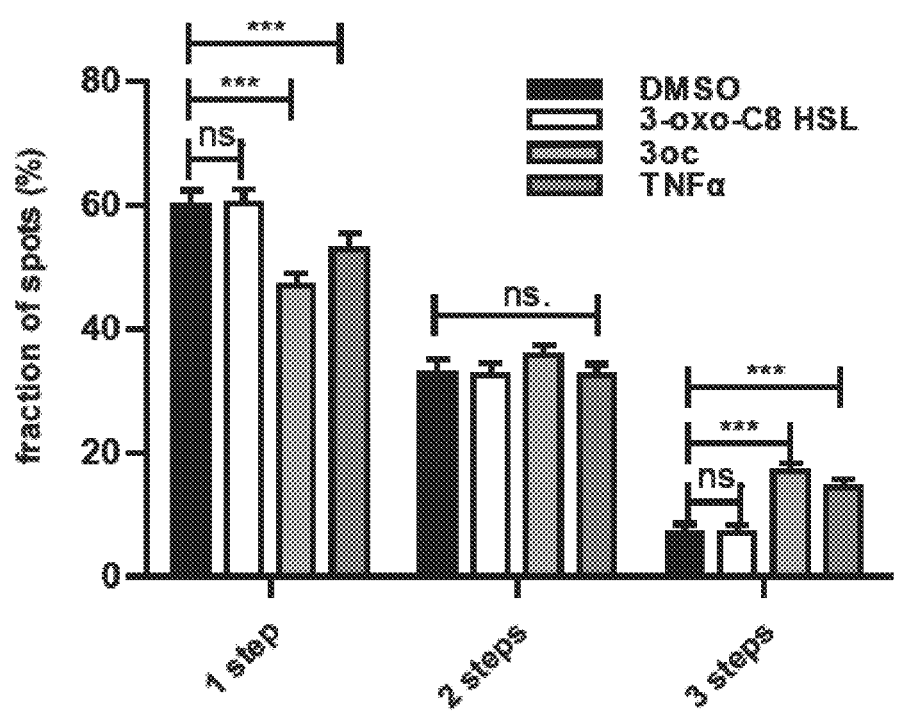
Figure 10A:
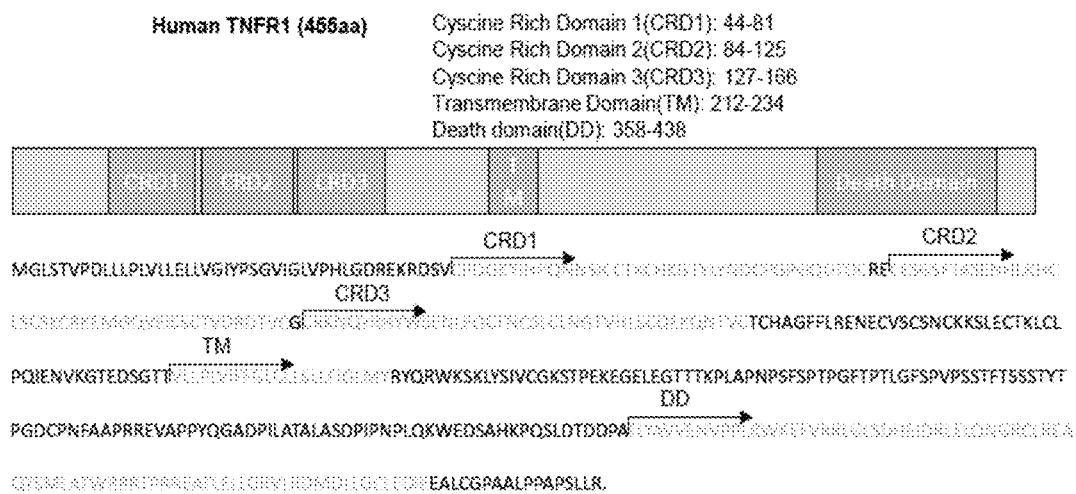
FIG. 10 shows Human TNFR1 domain illustration.
Figure 10B:
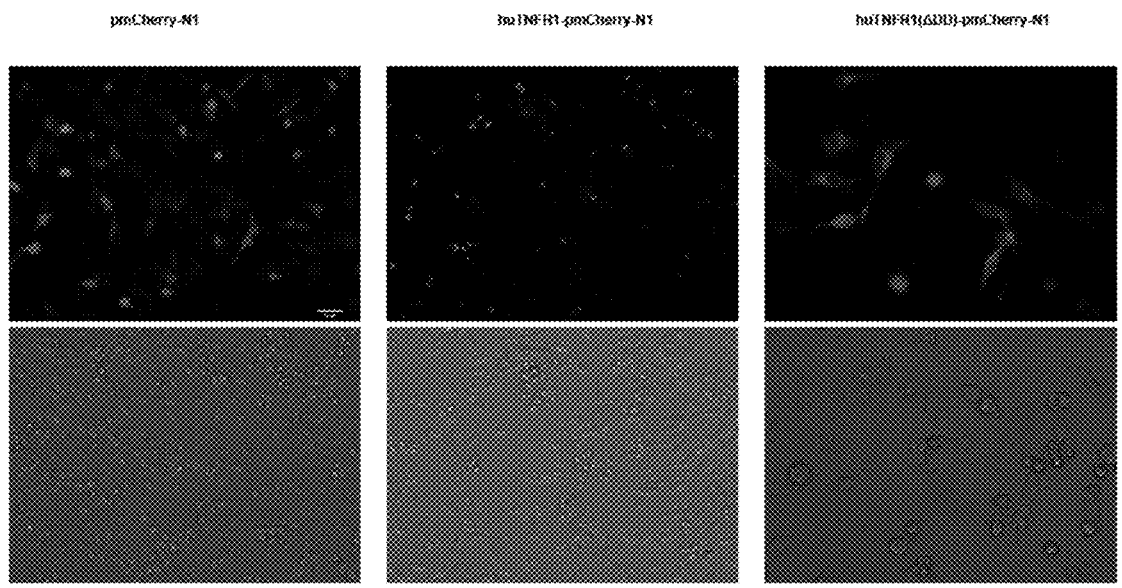
Figure 11:
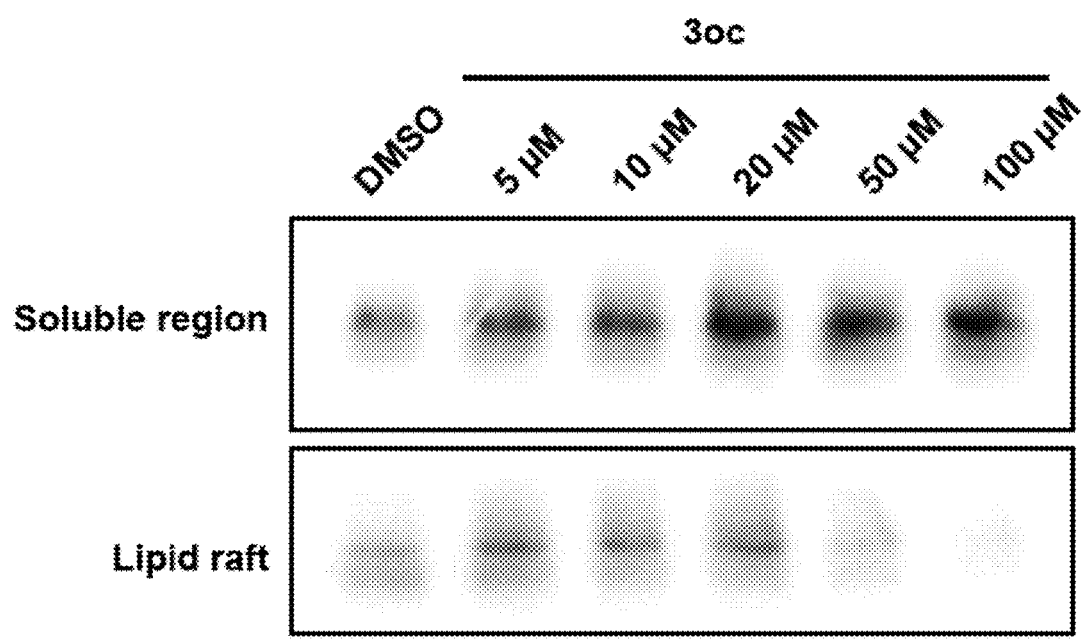
FIG. 11 shows 3OC12 HSL induces TNFR1 translocate to non-lipid raft region.

To rule out that 3OC12 HSL changed the condition of extraction which might result in artificial aggregation of TNFR1, multiple step fluorescence quenching (MSFQ) assay was performed to analyze TNFR1 in its native state on the membrane (FIG. 8b). Since addition of 3OC12 HSL leads to TNFR1-dependent cell death, a mutant TNFR1 with DD domain deleted and an addition of eGFP or mCherry sequence at its cytosolic terminus was transfected into HELA cells (FIG. 10a). Transfectants with modest fluorescence signal were selected (for MSFQ optimization, FIG. 10b). Addition of 3OC12 HSL increased the percentage of three step quenching pattern, confirming that the trimerization was induced. Statistical analysis shows that the one step bleaching frequency changed from 60.0+/−2.4% to 47.1%+/−1.9% ($p<0.001$), while the three step increased from 7.1+/−1.4% to 17.0+/−1.3% ($p<0.001$) (FIG. 8c). This trimerization similarly occurred in the presence of TNFα, yet failed to increase in response to 3OC8 HSL, a non-death-inducing analog, confirming the ligand binding equivalency by 3OC12 HSL treatment (FIG. 8c). The inventors found that in both human and mouse T cells, TNFR1 associated with lipid rafts, as represented by the quantity in detergent resistant domains, was reduced in the presence of 3OC12 HSL (FIG. 11).

Figure 12A:
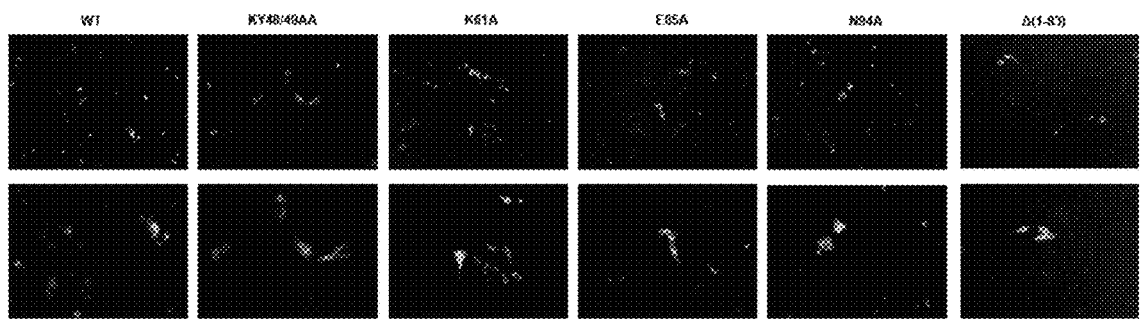
FIG. 12 shows Effects of mutations of critical amino acids in TNFR1 extracellular domain on 3OC12 HSL-induced TNFR1 trimerization.
Figure 12B:
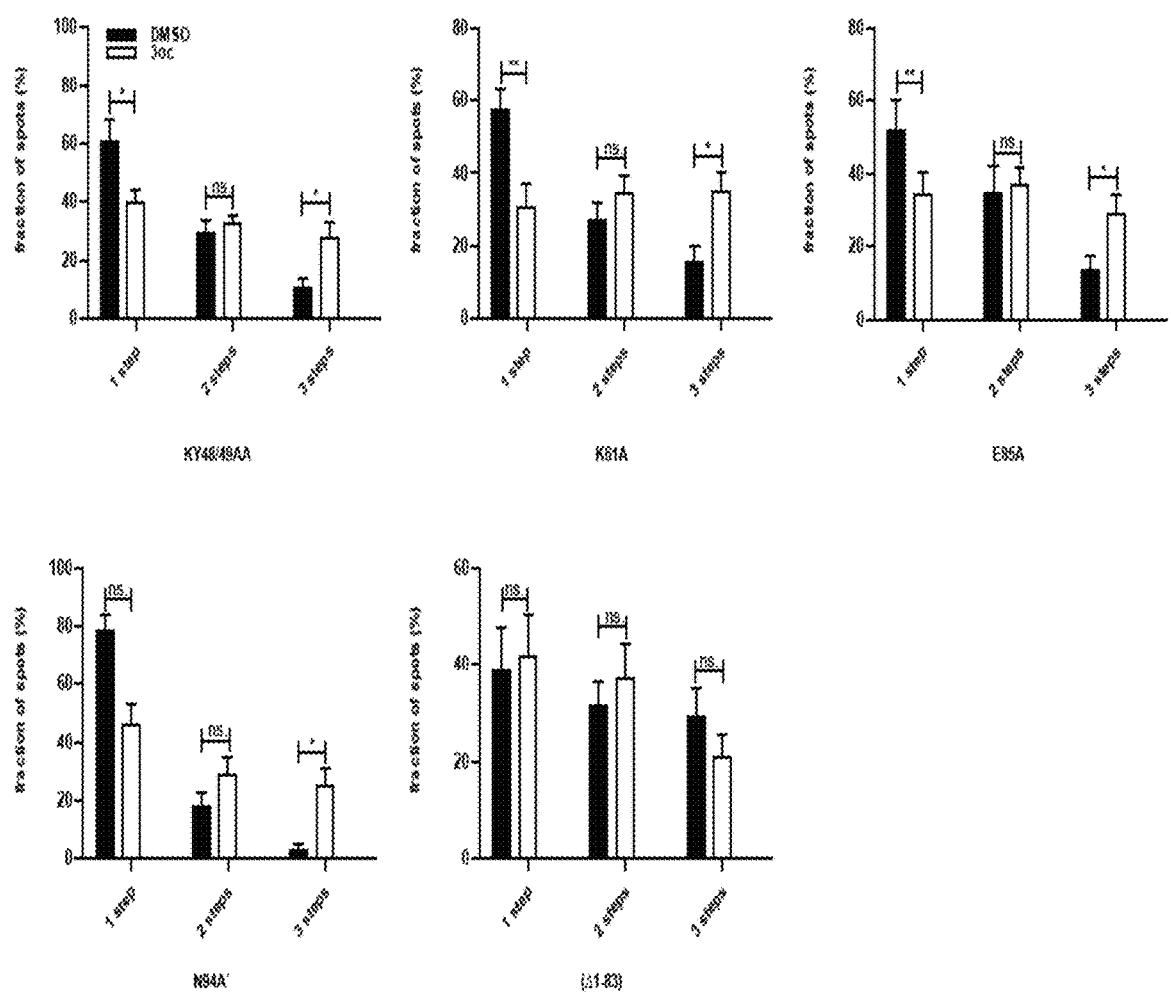

Baseline trimerization of TNFα has been proposed to be a threshold setter for its signaling, a feature related to its CRD1 domain. Ligand-induced trimerization, however, is mediated by the adjacent CRD2. To determine if 3OC12 HSL-mediated trimerization requires any of those domains, critical residues in CRD1 (KY48/49AA and K61A) and CRD2 (E85A and N94A) were mutated (FIG. 12a), and the MSFQ was performed to determine their association. Interestingly, none of these four mutants was individually essential for the multimerization associated with 3OC12 HSL (FIG. 12b). Only when the entire CRD1 was deleted, the impact of 3OC12 HSL treatment became insignificant (FIG. 12b).

Figure 8D:
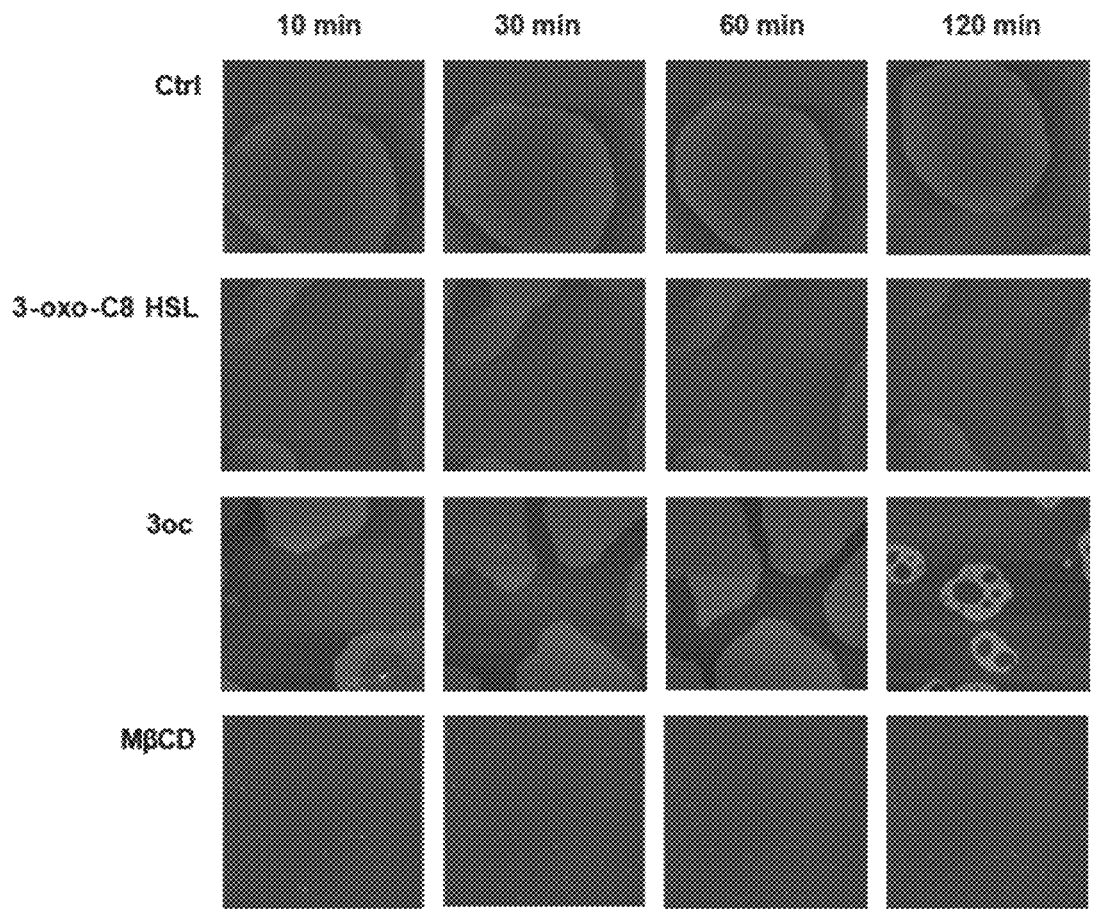
Figure 8E:
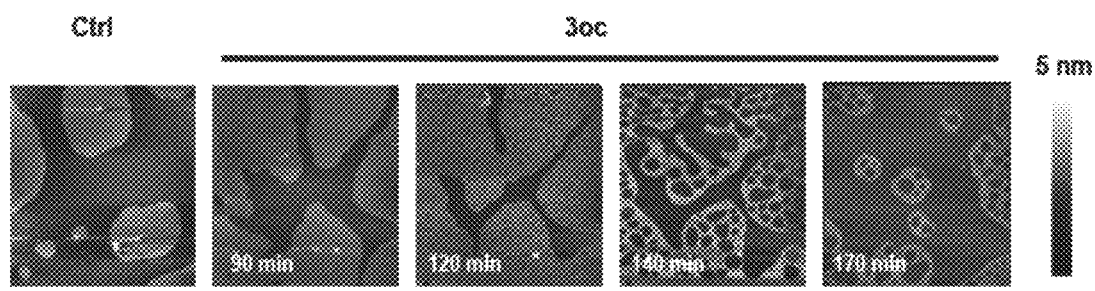
Figure 13A:
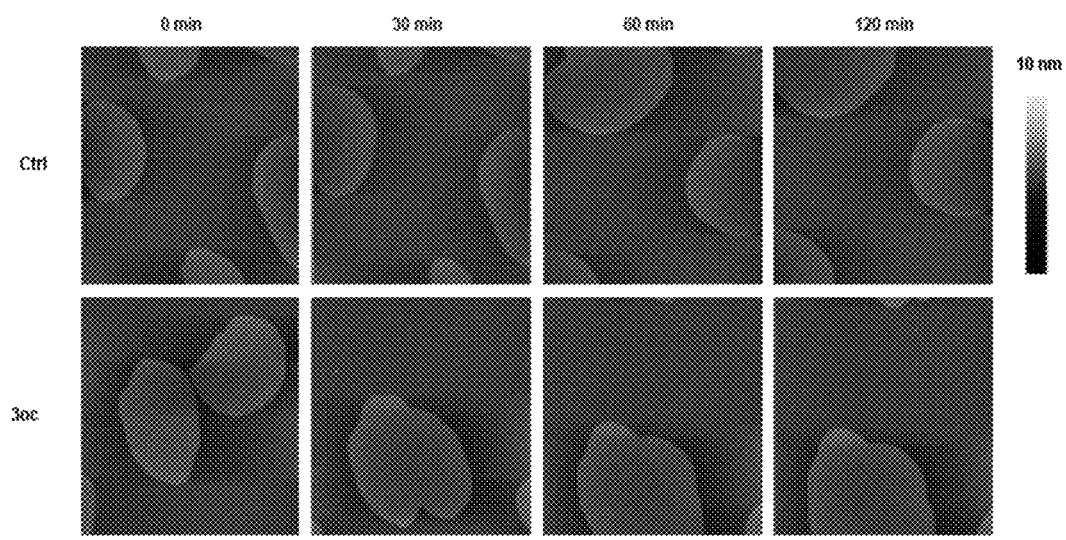
FIG. 13 shows Lipid domains in the presence of 3OC12 HSL.

Large lipid rafts can be reconstituted with extracts from membrane lipids 26. We studied the morphology of these domains in the presence of 3OC12 HSL. On the glass substrate under aqueous phase, the ordered lipid domains, determined by scanning mode of atomic force microscopy to be at least 1 nm thickness elevation over the surrounding membrane (FIG. 8d), were stable. 3OC12 HSL drastically changed the appearance of those domains with a clear dissolution of the elevated plains (FIG. 8d). This dissolution was initiated from the center of the domain with the porous presence increasing over time (FIG. 8e). In contrast, smaller domains formed with a mixture of DOPC and DPPG, unrelated to lipid rafts, were minimally affected (FIG. 13a), suggesting that the 3OC12 HSL specifically targets domains formed in the presence of cholesterol and sphingolipids.

Figure 8F:
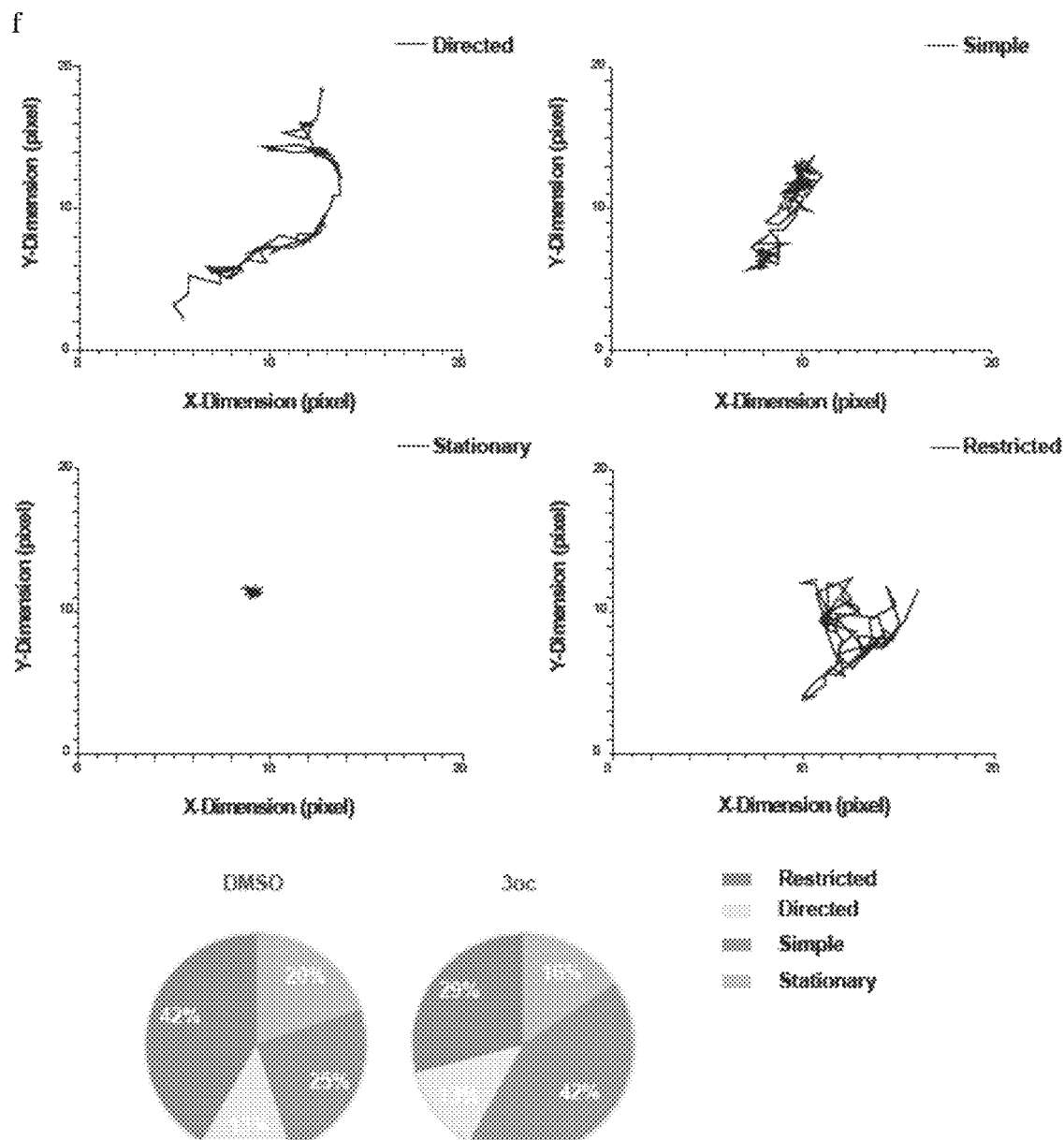
Figure 8G:
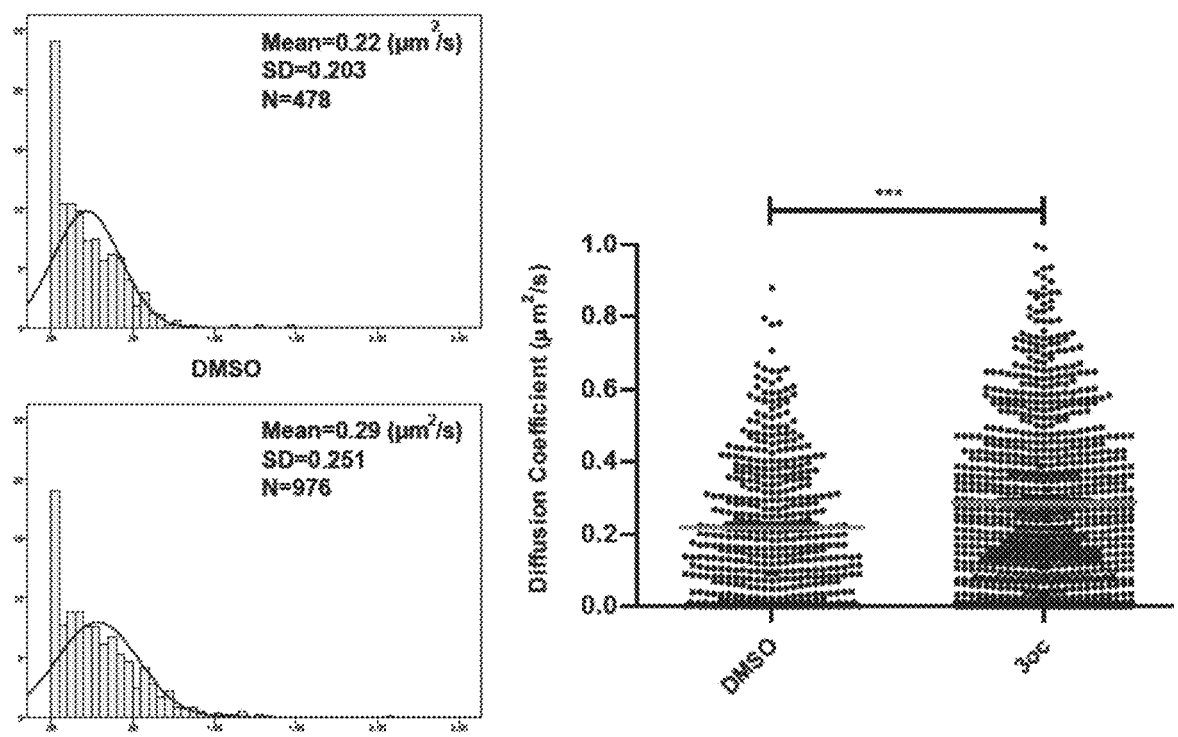
Figure 8H:
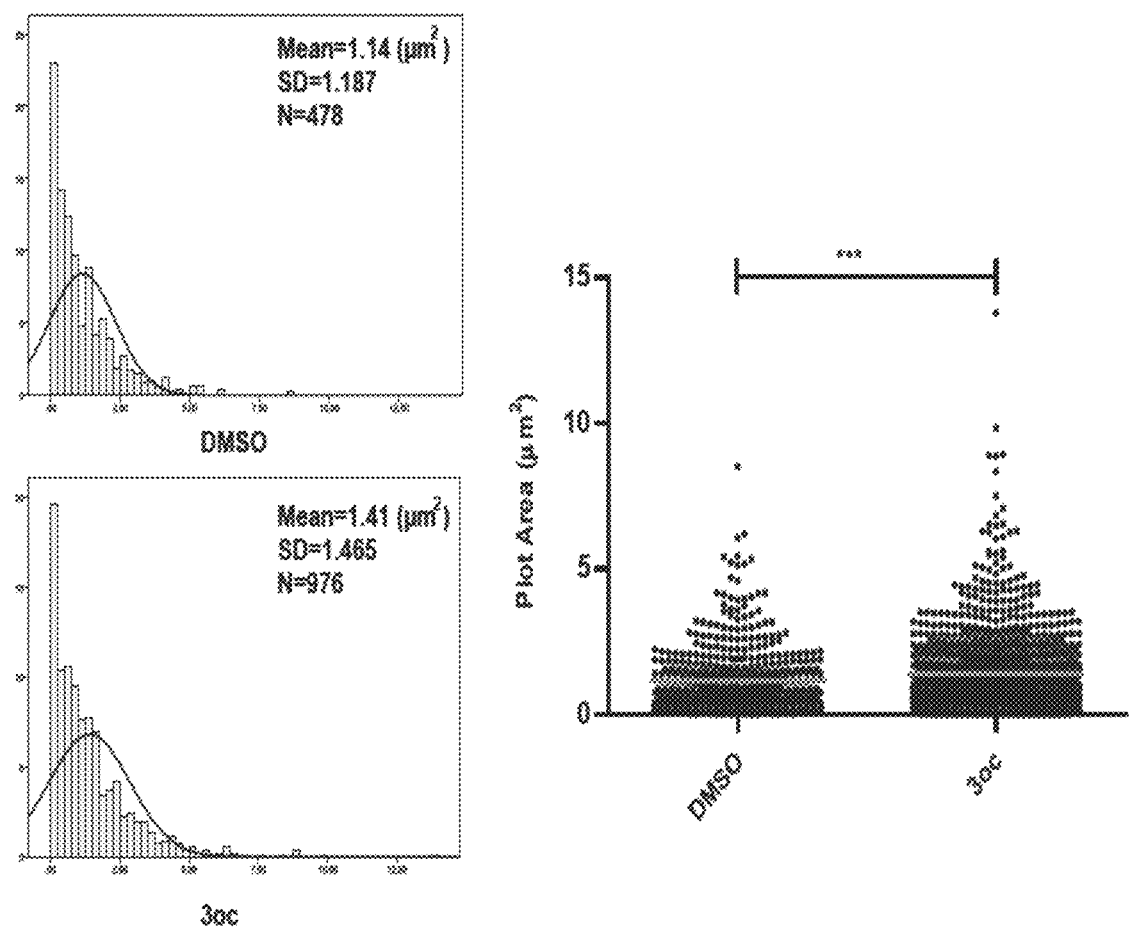
Figure 13B:
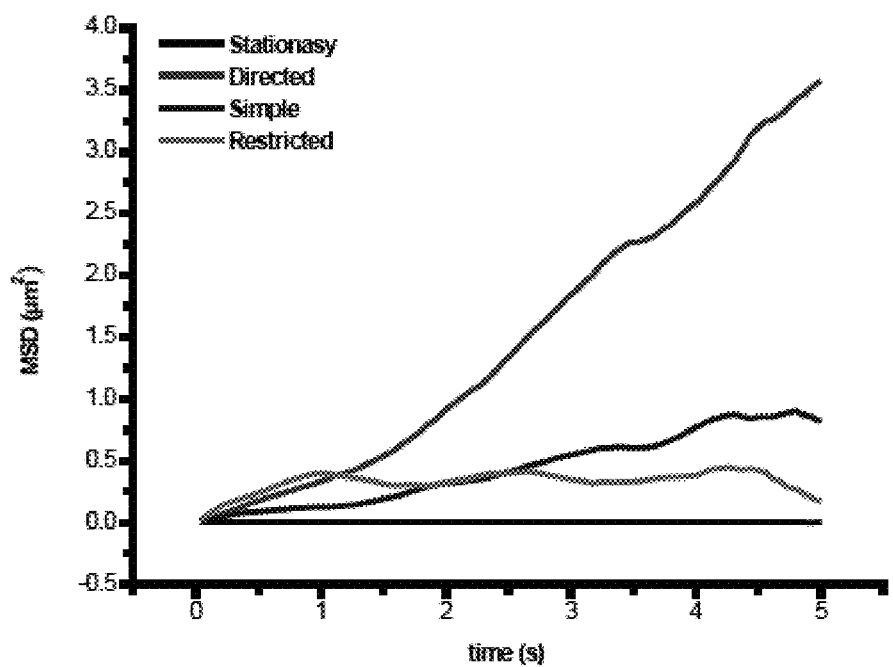
Figure 14A:
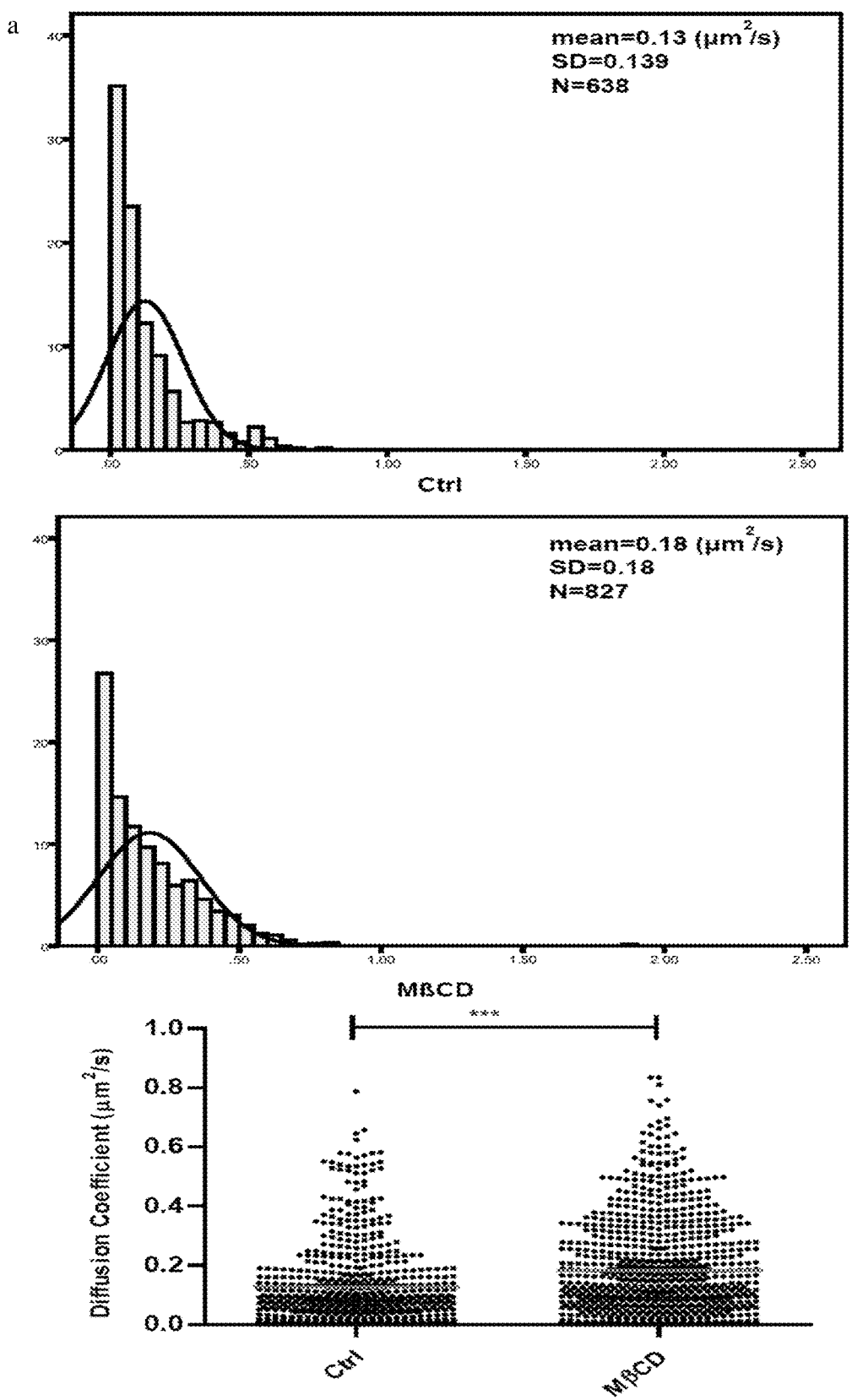
FIG. 14 shows MβCD has effects similar to those of 3OC12 HSL on the behavior of TNFR1 on the plasma membrane.
Figure 14B:
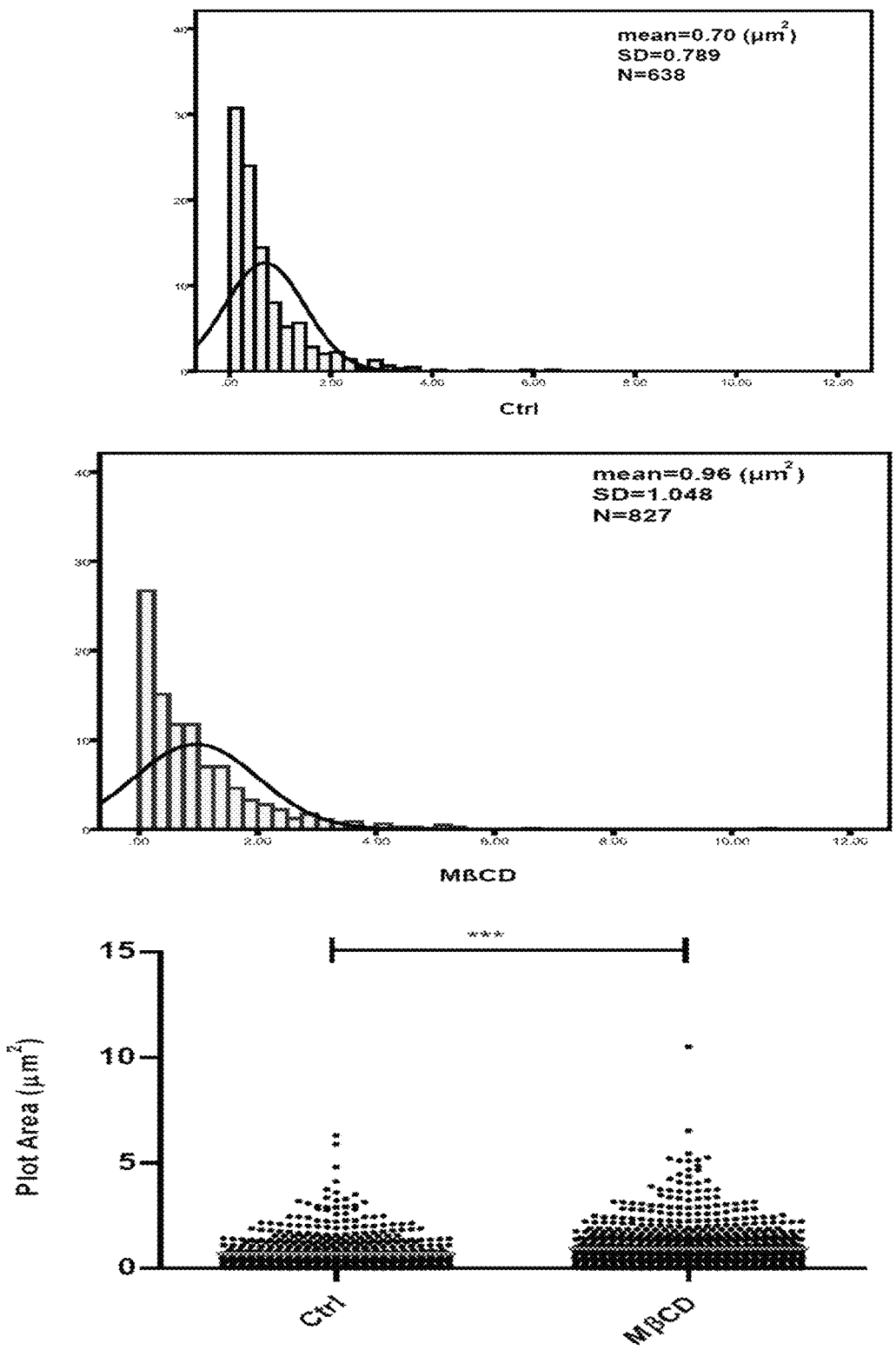

In recent years, a new proposal suggests that lipid disordered phases are more intertwined with cortical cytoskeleton, creating a physical barrier to confine ordered domains. This model has been experimentally verified with a STED-based imaging technique 30. Transmembrane proteins under this constrain display motion trajectories characterized as simple, directed, stationary and restricted. To determine the motion pattern of TNFR1 under 3OC12 HSL-mediated domain disruption, extracellular TNFR1-specific antibody was digested by papain to yield the Fab fragment to avoid receptor crosslinking. A streptavidin-linked quantum dot with 605 nm emission wavelength was fused to the purified Fab. TNFR1 motion patterns were derived from a series of movies. Motion trajectory of each label was fitted in a mean square distribution (MSD) analysis (FIG. 13b). The four patterns were obtained, as expected (FIG. 8f). With 3OC12 HSL, TNFR1 was more likely to fall into the simple mode of motion with a reciprocal drop in the restricted and stationary patterns (FIG. 8f). Accordingly, the diffusion coefficient also significantly increased (FIG. 8g), implicating a higher diffusibility of TNFR1 in a "domain-less"

plasma membrane. In the treated membrane, each individual TNRF1 showed high x-y surface area coverage (FIG. 8h). The inventors attempted to approximate this higher diffusibility with MβCD (FIG. 8d last row). As expected MβCD treatment qualitatively recaptured the essence of 3OC12 HSL, rendering TNFR1 with a higher diffusion coefficient and a larger area coverage (FIGS. 14a and b).

Figure 15A:
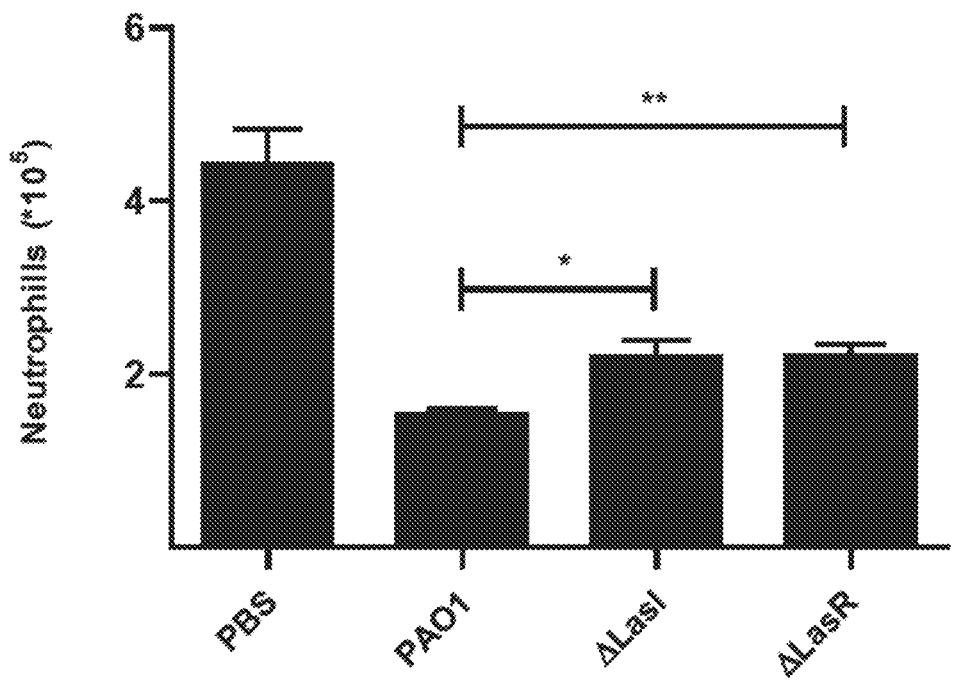
FIG. 15 shows 3OC12 HSL induced extrinsic apoptosis promotes PA infection and alters other receptor behaviors on plasma membrane.
Figure 15B:
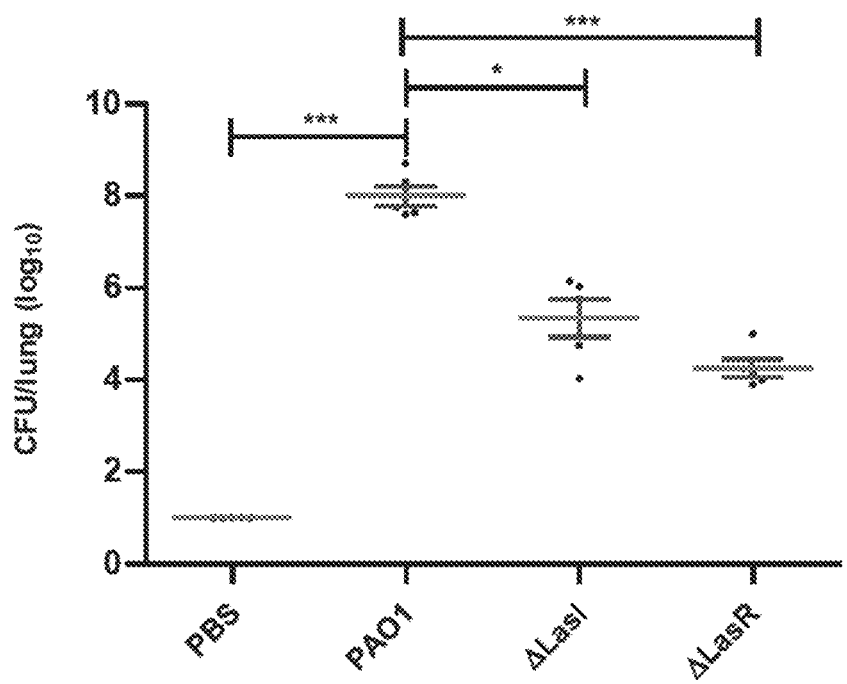
Figure 15C:
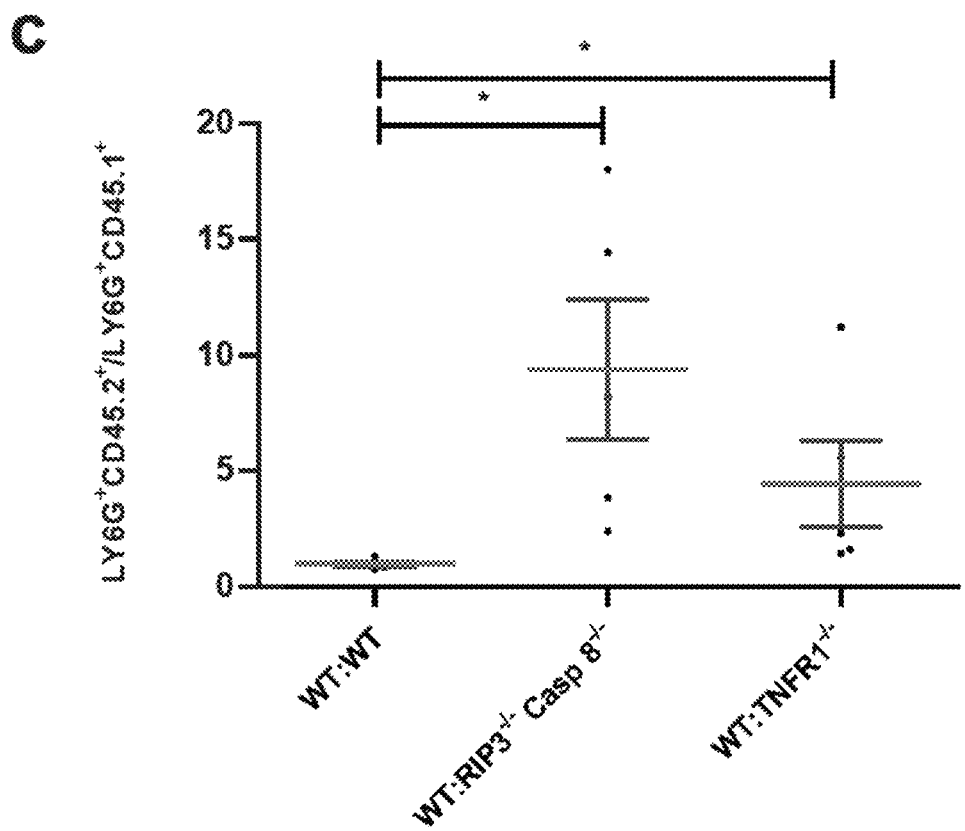
Figure 15D:
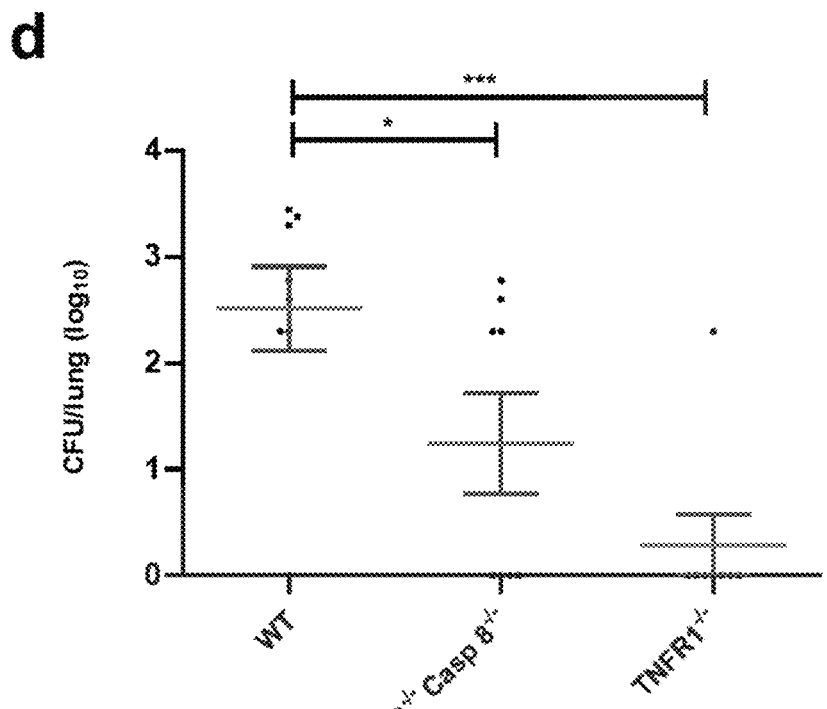
Figure 15E:
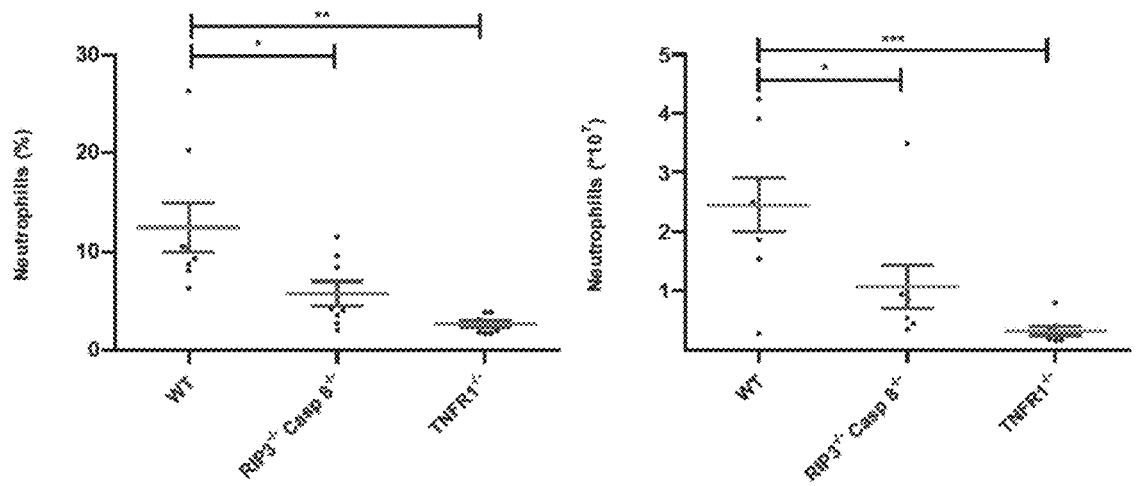
Figure 15F:
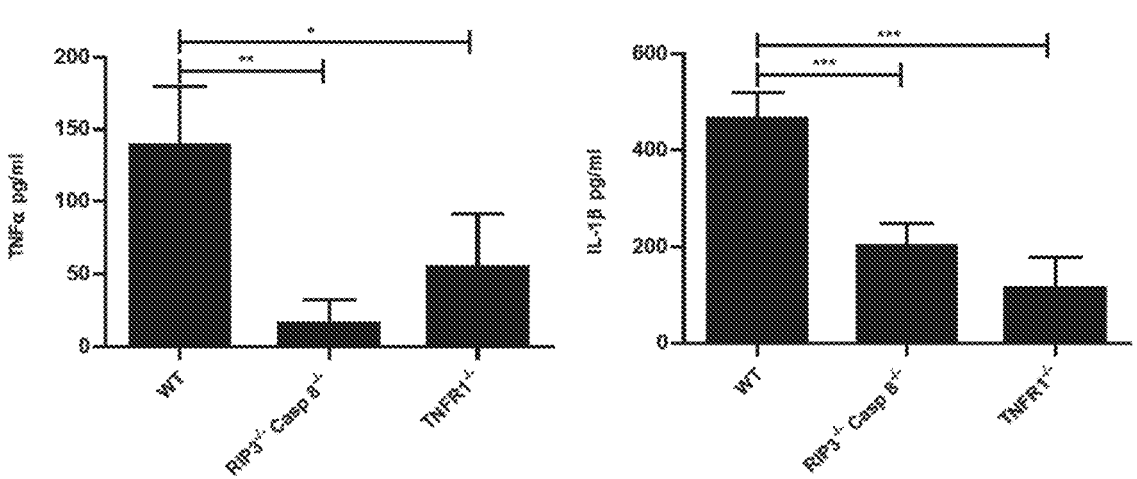
Figure 16A:
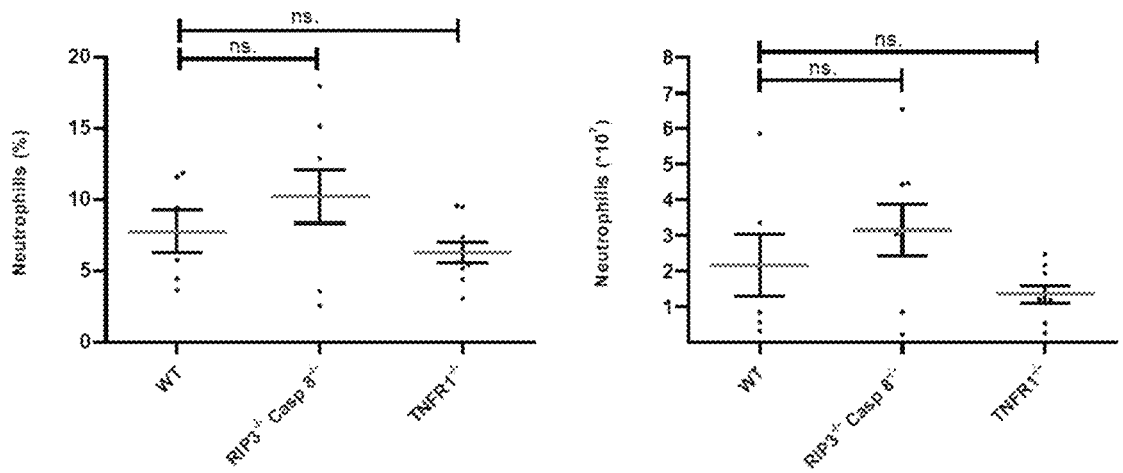
FIG. 16 shows TNFR1 signaling pathway is dispensable for the severity of acute PA infection in the absence of 3OC12 HSL.
Figure 16B:
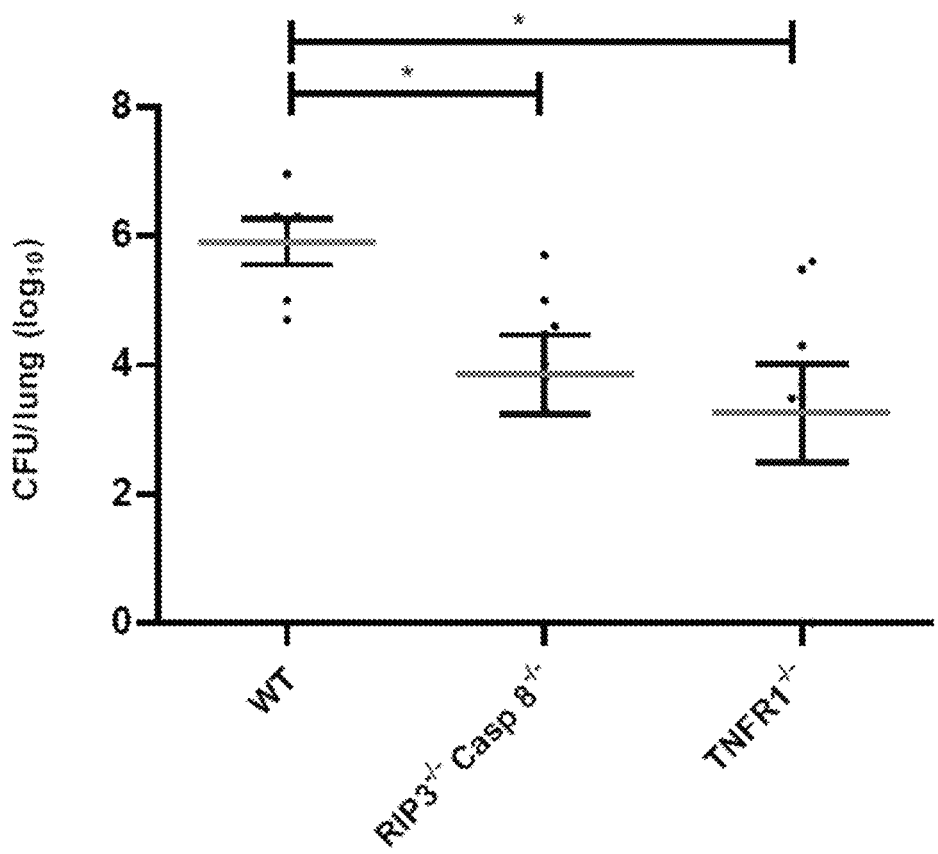

HSLs have been regarded as virulence factors via bacterial collective activities 33. As the inventors' results suggest a definable host response to 3OC12 HSL, the inventors wondered whether its virulence can be additionally explained by reduced host defense via immune suppression. The inventors cultured neutrophils from C57BL/6 mice with supernatants of wild type (PAO1), LasI-deficient (ΔLasI) and LasR deficient (ΔLasR) PA cultures. As is shown in FIG. 15a, either deficiency in the Las circuitry resulted in significant reduction in cell loss. To further confirm the result, the inventors i.t. inoculated C57BL/6 mice with PAO1, and ΔLasI and ΔLasR PA. Lung extracts from the mutant-infected mice showed reduced PA CFUs (FIG. 15b). The results suggested that 3OC12 HSL was a virulence factor by directly suppressing host immune response using host's own TNFR1 pathway. To isolate this possibility from its role in the QS itself, we reconstituted γ-irradiated CD45.2 C57BL/6 mice with hybrid bone marrow cells composed of CD45.1 (wild type) and CD45.2 (wild type or Casp8−/− or Tnfrsf1a−/−), and challenged the recipients with PAO1 strain. FIG. 15c shows that Casp8−/− and Tnfrsf1a−/− neutrophils had higher resistance to 3OC12 HSL-induced apoptosis than did wild type neutrophils. Accordingly, the mutant recipients showed better clearance of the infection as measured by the CFUs in the lung extracts (FIG. 15d). FIGS. 15e and *f* show that the lack of 3OC12 HSL-mediated apoptosis in these mice significantly reduced the neutrophil infiltration and TNFα and IL-1β production, implying a more efficient response. Inoculation of LasI-deficient PA strain had little difference in neutrophil counts between wild type and Casp8−/− or Tnfrsf1a−/− bone morrow reconstituted mice (FIG. 16a), and the PA CFU count differences became smaller compared with PAO1 inoculation (FIG. 16b), strengthening the specific targeting of TNFR1 pathway by 3OC12 HSL in vivo.

Figure 15G:
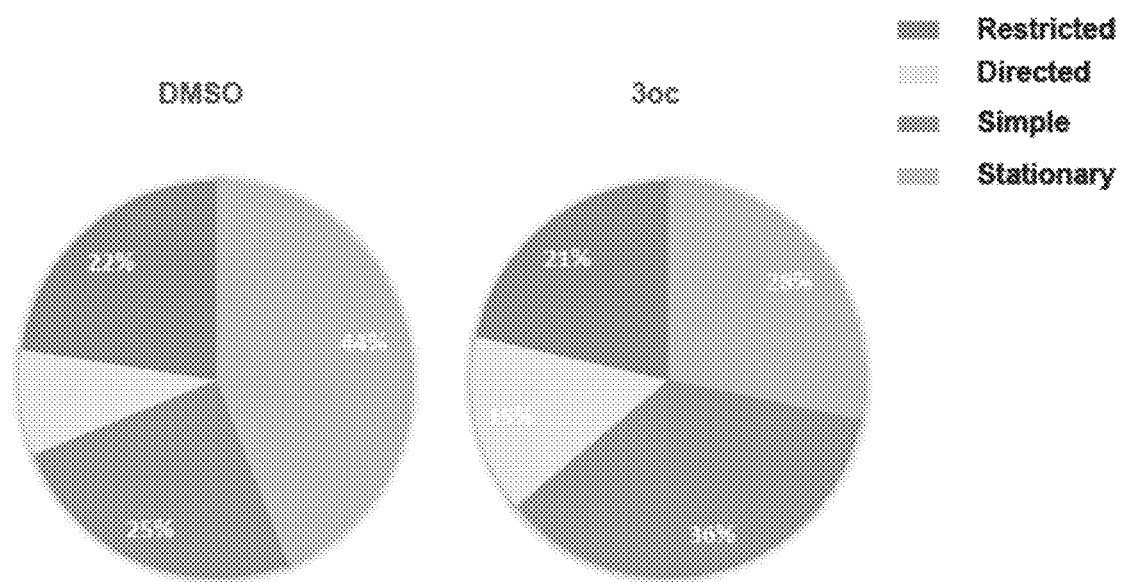
Figure 15H:
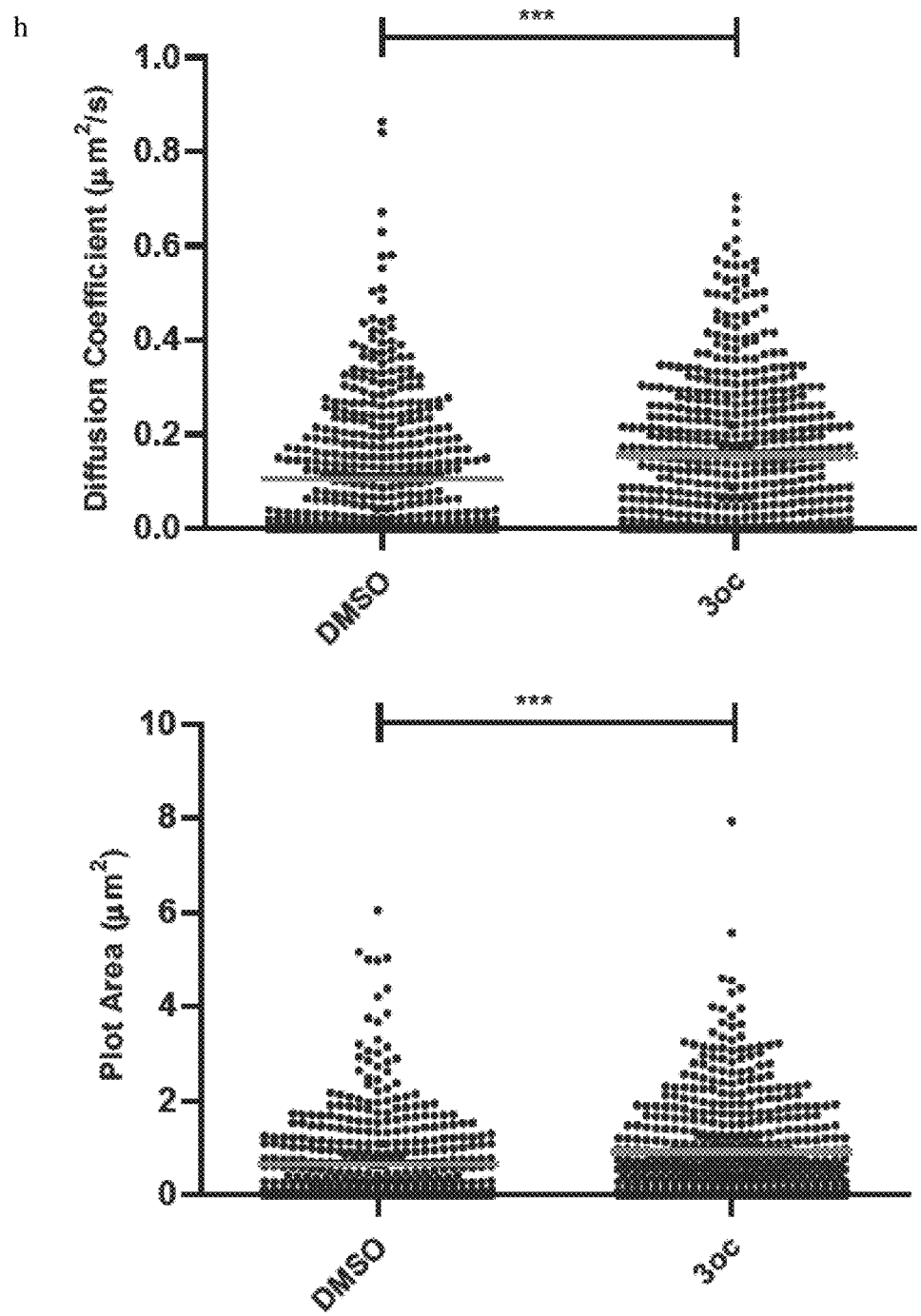
Figure 15I:
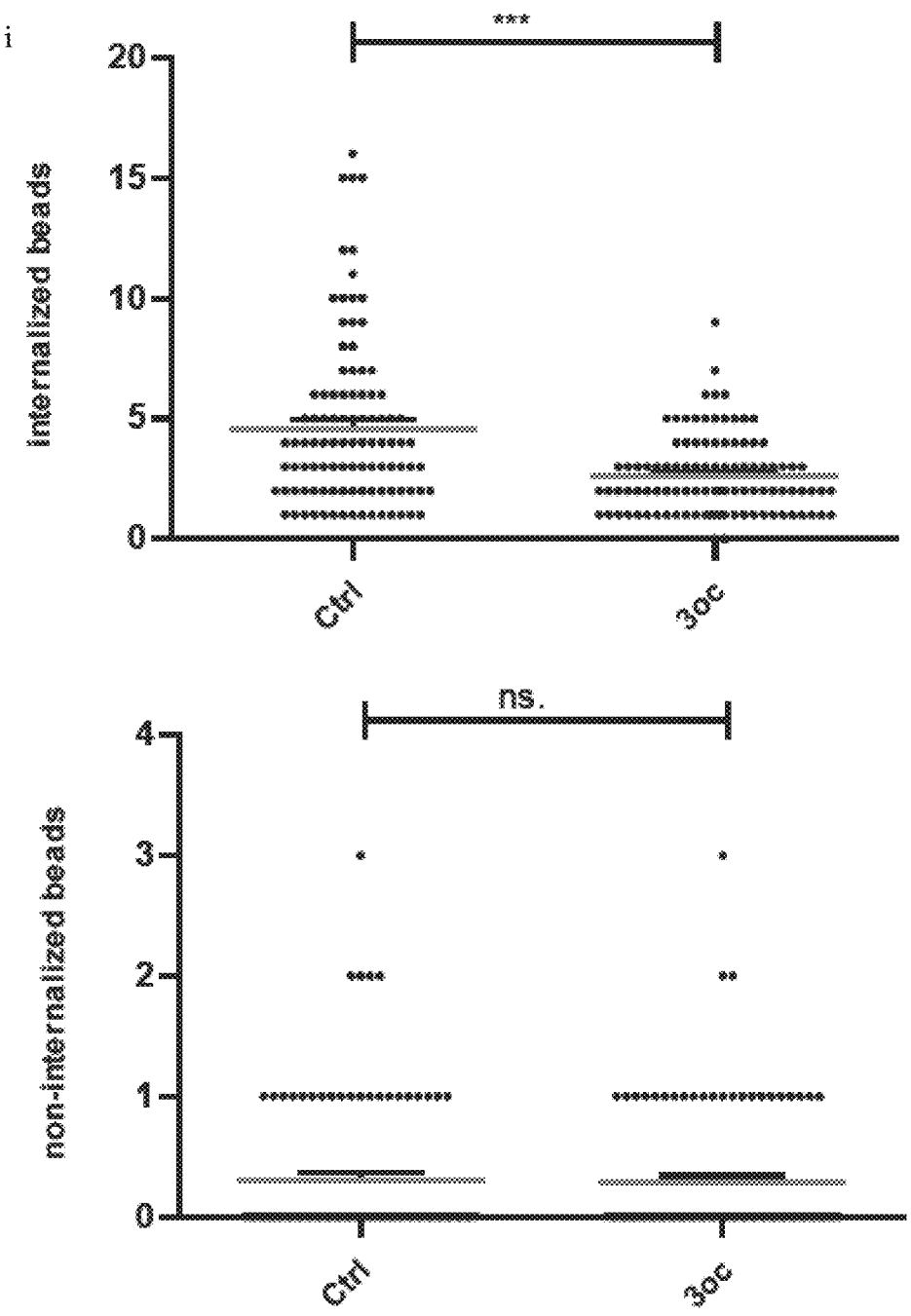
Figure 15J:
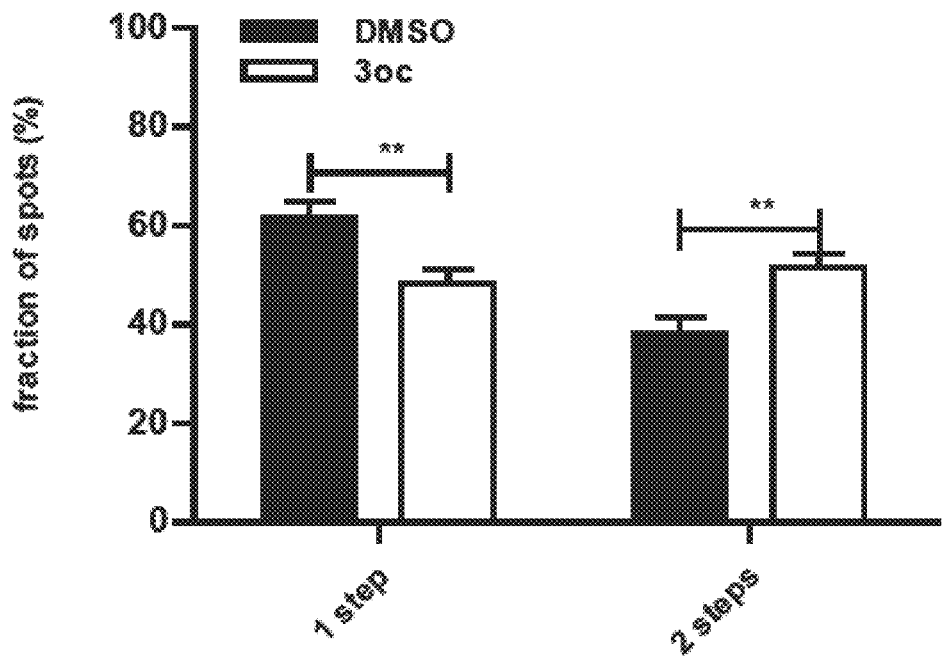
Figure 15K:
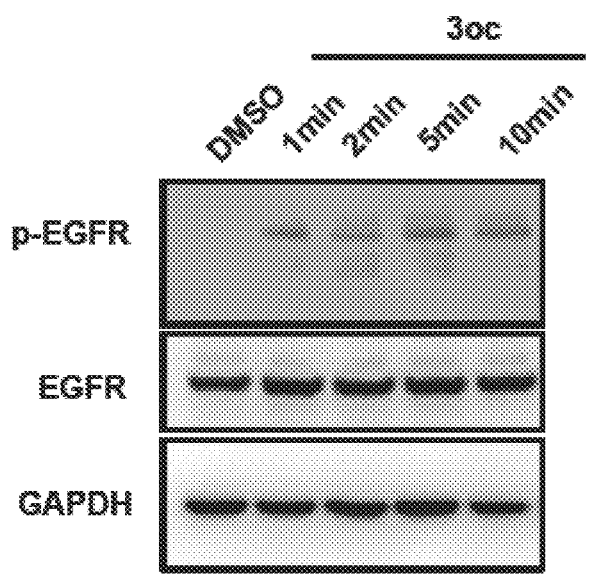

The proceeding results show that mixing of 3OC12 HSL in mammalian plasma membrane has overt consequences in TNFR1 signaling. A question arose whether 3OC12 HSL could modulate other surface receptor behaviors in the treated membrane, particularly in TNFR1-negative cells or those with preferential pro-survival signaling. The inventors first analyzed human Fcγ RIIA, a low affinity Fcγ receptor with an intrinsic cytoplasmic ITAM domain 34. In Cos-1 cells transfected with Fcγ RIIA, the quantum dot-based single particle tracking was performed. The results show that a higher percentage of Fcγ RIIA belonged to the simple and directed motions with a simultaneous reduction in the stationary mode following 3OC12 HSL treatment (FIG. 15g). With 3OC12 HSL, this receptor also showed a higher diffusion coefficient (0.1056+/−0.006 vs 0.1564+/−0.006, p<0.001) and a larger area covered by its motion tracks (0.6467+/−0.042 vs 0.9310+/−0.045, 10p<0.001) (FIG. 15h). As Fcγ R signaling is also regulated by the membrane domain association, the inventors found that while attachment to the cells was similar, phagocytosis of antibody-coated latex beads was reduced by 3OC12 HSL (4.6+/−0.3% vs 2.6+/−0.2%, p<0.001) while the attachment of beads to those cells were not affected (FIG. 15i). For EGFR, a non-immune membrane receptor with its signaling dependent on lipid domain association 35, we performed the MSFQ to determine whether 3OC12 HSL altered its base frequency of dimerization. FIG. 15j shows 3OC12 HSL increased the dimerization in comparison with the carrier treatment. As a result, EGFR phosphorylation became detectable in the absence of the ligand (FIG. 15k). Collectively, these data implicate a generic disruption of host cell surface receptor signaling by the simple presence of 3OC12 HSL in the plasma membrane.

Figure 17A:
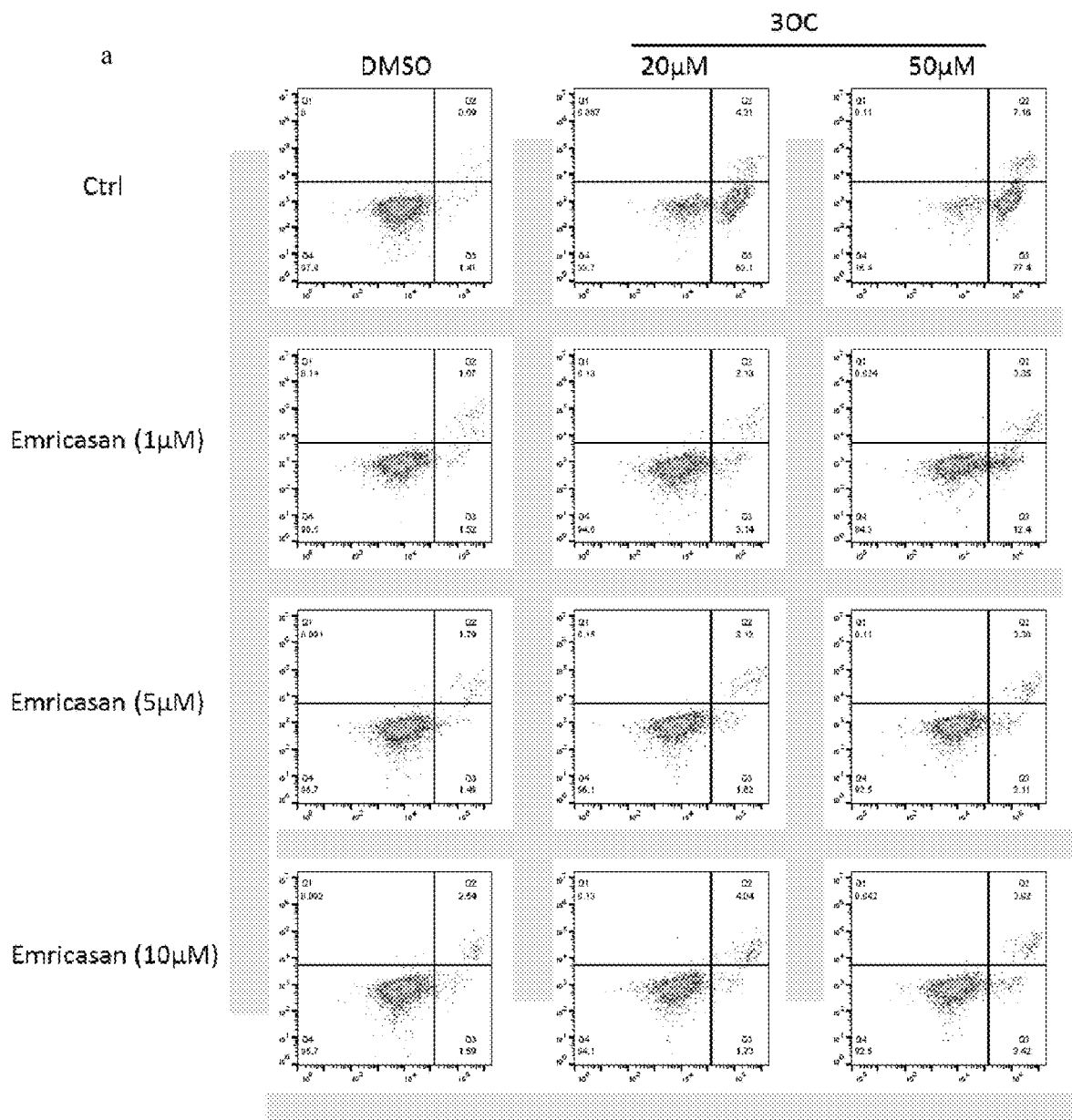
FIG. 17 shows Emricasan in blocking 3OC12-HSL's apoptotic effect in human THP-1 cell line and mouse splenocytes.
Figure 17B:
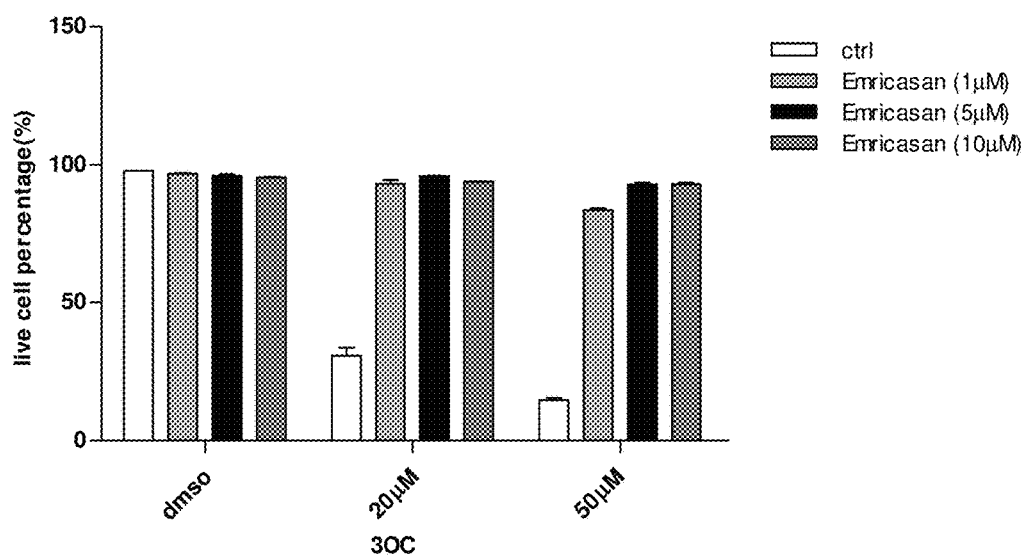
Figure 17C:
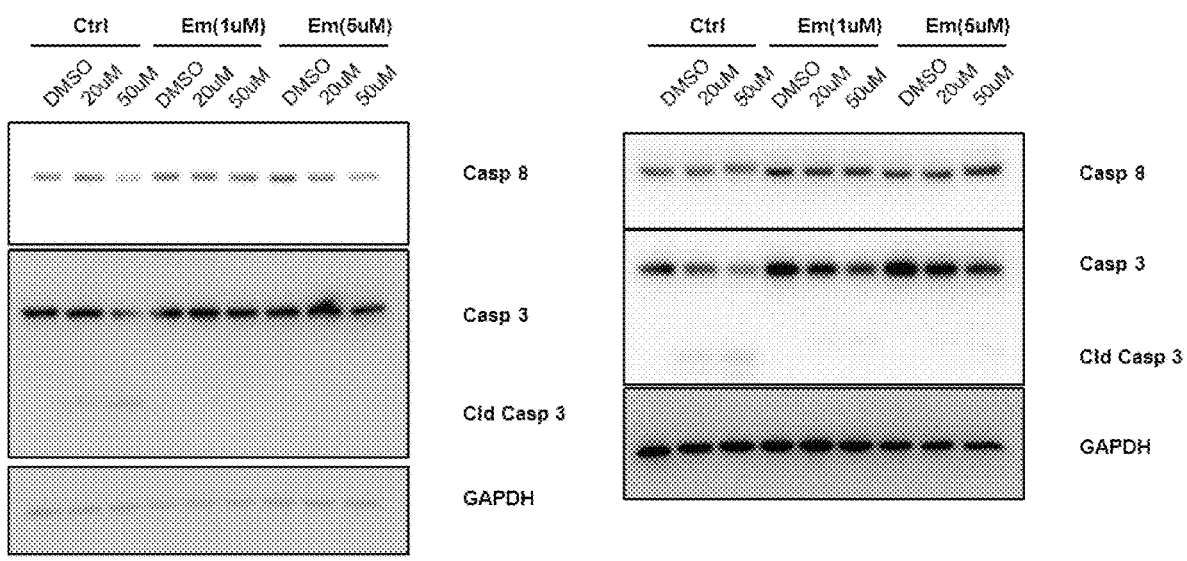
Figure 17D:
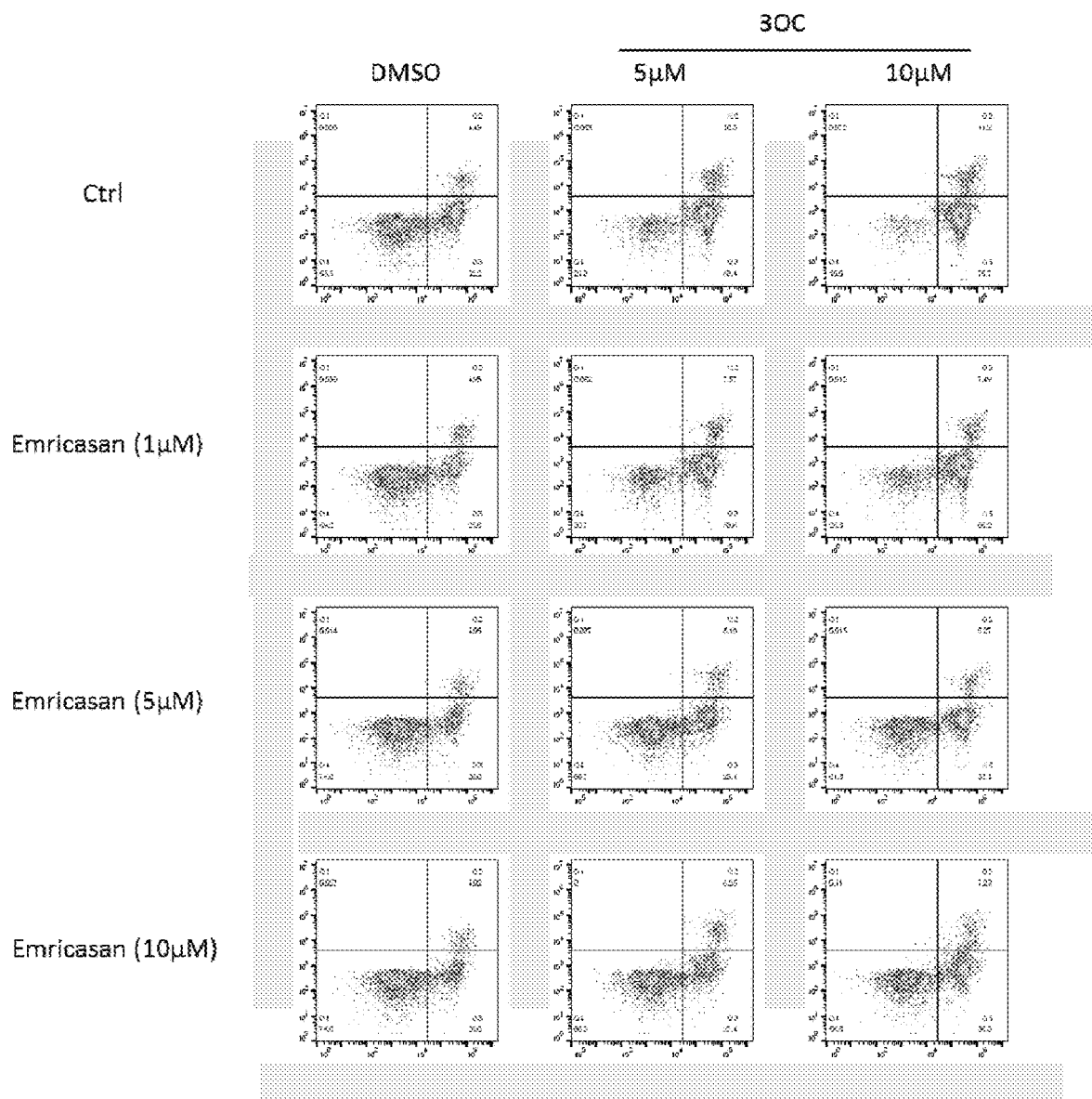
Figure 17E:
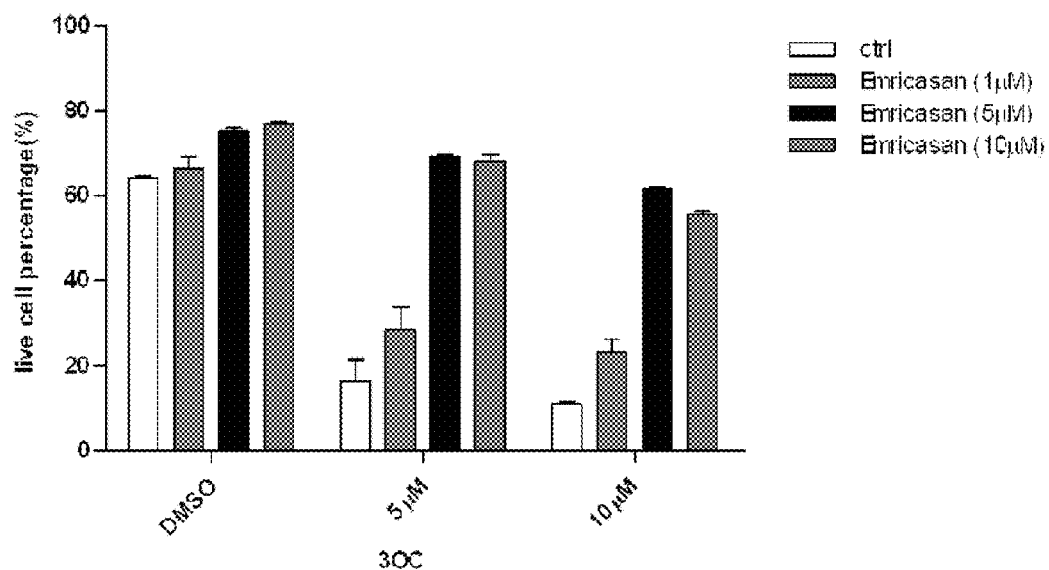
Figure 17F:
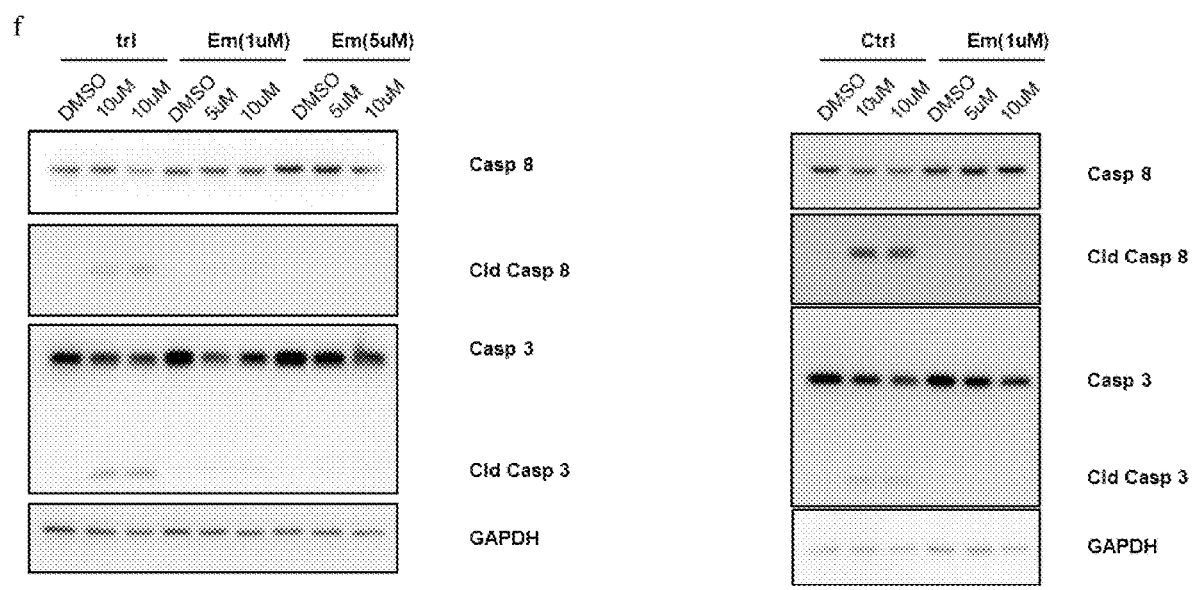

In order to verify TNFR1-FADD-caspase8-caspase3 pathway inhibitor can block immunocyte apoptosis caused by 3OC12-HSL clinically. The inventors use a clinical version of caspase inhibitor Emricasan as a test. Through standard AnnexinV and PI staining experiments, the inventors found surprisingly that the clinical version of caspase inhibitor Emricasan has good effect in blocking 3OC12-HSL's apoptosis in mouse splenocytes and human THP-1 cell line. The results are showed as FIG. 17a~FIG. 17f. Wherein, FIG. 17a shows the flow cytometric analysis of apoptosis staining in THP-1 cell line. To be specific, in a 12 plate, THP-1 cells were cultured with indicated concentrations of 3OC and Emricasan. After 1 hr, cells were collection for flow cytometric analysis of AnnexinV and PI. FIG. 17a shows that Emricasan has good effect in blocking 3OC12-HSL's apoptosis in human THP-1 cell line. FIG. 17b shows the statistical result of flow cytometric analysis of apoptosis staining of FIG. 17a. In FIG. 17b, live cell percentage of different treatment were enumerated by flow cytometry. Bar graphs of live cell percentage are depicted by mean±SEM. Then samples prepared as in FIG. 17a and FIG. 17b were used for WB analysis for the activation (cleavage) of Caspase 8 and 3. The results are showed as FIG. 17c. In FIG. 17c, the incubate time of the left panel is 1 hr, and the left panel is 2 hr. (Casp 8: Caspase 8, Cld Casp 8: Cleaved-Caspase 8, Casp 3: Caspase 3, Cld Casp 3: Cleaved-Caspase 3). FIG. 17c shows that Emricasan has effect in blocking 3OC12-HSL's apoptosis mediated by Caspase in human THP-1 cell line. Furthermore, the inventors use B6 splenocytes (separated from C57BL/6 spleen) as the test. The results are showed as FIG. 17d~FIG. 17f. FIG. 17d~FIG. 17f. shows that Emricasan aslo has good effect in blocking 3OC12-HSL's apoptosis in B6 spleenocytes.

X-box-binding protein 1, PPAR β/δ and PPARγ were suggested to 3OC12 HSL's activities. More likely to be secondary signaling events, those molecules are not known to serve as direct targets of the autoinducers. In this report, the inventors show that the sensing of this bacterial metabolite is via the membrane disturbance, thus broadly altering mammalian cell surface, with apoptosis being the most discernable consequence in some cells.

The demarcation of prokaryotic and eukaryotic systems is defined by several universal features. Unique in eukaryotic cells, membrane domains are a feature supported by the miniature crystal-like aggregation of sphingo lipids and cholesterol that are absent in bacterial world. In addition, dynamic lipid domains form picket fence-like arrangements constrained by adherence of long chain phospholipids to the underlying cortical cytoskeleton. The dynamic association of receptors with these domains is a regulatory mechanism to control signals transmitted through these molecules. This feature renders the eukaryotic membrane particularly sensitive to lipid domain disruption, in a sharp contrast with bacterial membrane with a relatively fixed peptidoglycan-based cell wall sandwiched by two double Singer-Nicolson bilayers that characteristically lack sterols (such as cholesterol).

A surprising finding of this work is that PA uses 3OC12 HSL to disarm the immunity via directly triggering host's own TNFR1 signaling, causing early responding neutrophils to undergo apoptosis, in favor of bacterial survival. This result exposes an immune regulatory mechanism by the autoinducer that is directly coupled to the signaling in host cell defense. This finding and the revelation that bacterial autoinducers use a previously unknown inter-kingdom communication method to regulate host innate immunity provide important insights into a new innate sensing mechanism and a definable target for clinical control of *Pseudomonas* infection.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A method for treating an immune system related disease caused by an autoinducer, comprising:
   administrating a TNFR1-FADD-caspase8-caspase3 pathway inhibitor to a subject in need thereof,
   wherein the TNFR1-FADD-caspase8-caspase3 pathway inhibitor is a TNFR1 trimerization inhibitor or Emricasan,
   wherein the immune system related disease is *Pseudomonas aeruginosa* infection-related disease, and
   wherein the autoinducer is derived from *Pseudomonas aeruginosa* and is $C_{10\sim12}$ alkyl acyl homoserine lactone.

2. The method of claim 1, wherein the TNFR1 trimerization inhibitor comprises:
   (a) a competitive inhibitor peptide for TNFR1; or
   (b) a nucleic acid or construct expressing (a).

* * * * *